(12) United States Patent
McCray, Jr. et al.

(10) Patent No.: US 7,439,066 B2
(45) Date of Patent: Oct. 21, 2008

(54) METHODS FOR PRODUCING AND USING IN VIVO PSEUDOTYPED RETROVIRUSES USING ENVELOPE GLYCOPROTEINS FROM LYMPHOCYTIC CHORIOMENINGITIS VIRUS (LCMV)

(75) Inventors: Paul B. McCray, Jr., Iowa City, IA (US); Beverly L. Davidson, North Liberty, IA (US); Colleen Stein, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/593,963

(22) Filed: Nov. 7, 2006

(65) Prior Publication Data

US 2007/0059291 A1    Mar. 15, 2007

Related U.S. Application Data

(63) Continuation of application No. 10/993,319, filed on Nov. 19, 2004, now Pat. No. 7,160,727, which is a continuation-in-part of application No. 10/718,262, filed on Nov. 20, 2003, now Pat. No. 7,135,339.

(51) Int. Cl.
| | |
|---|---|
| C12N 15/87 | (2006.01) |
| C12N 15/88 | (2006.01) |
| C12N 15/867 | (2006.01) |
| C12N 5/10 | (2006.01) |
| A61K 48/00 | (2006.01) |

(52) U.S. Cl. .................... 435/458; 435/455; 435/456; 435/325; 435/368; 435/320.1

(58) Field of Classification Search .................. None
See application file for complete search history.

(56) References Cited

U.S. PATENT DOCUMENTS

| | | | |
|---|---|---|---|
| 5,512,421 A | 4/1996 | Burns et al. | |
| 5,643,756 A | 7/1997 | Kayman et al. | |
| 5,654,195 A | 8/1997 | Sodroski et al. | |
| 5,670,354 A | 9/1997 | Burns et al. | |
| 5,693,509 A | 12/1997 | Cotten et al. | |
| 5,711,964 A | 1/1998 | Dattagupta et al. | |
| 5,739,271 A | 4/1998 | Sridhar et al. | |
| 6,440,730 B1 | 8/2002 | Von Laer et al. | |
| 6,531,123 B1 | 3/2003 | Chang | |
| 6,555,107 B2 | 4/2003 | Poeschla et al. | |
| 6,589,763 B1 | 7/2003 | Von Laer et al. | |
| 7,135,339 B2 | 11/2006 | McCray, Jr. et al. | |
| 7,160,727 B2 * | 1/2007 | McCray et al. | 435/456 |
| 2003/0054548 A1 | 3/2003 | Kaleko et al. | |
| 2005/0112096 A1 | 5/2005 | McCray, Jr. et al. | |
| 2005/0123517 A1 | 6/2005 | McCray, Jr. et al. | |

FOREIGN PATENT DOCUMENTS

| | | |
|---|---|---|
| EP | 1 006 196 | 6/2000 |
| WO | WO 98/44788 | 10/1998 |
| WO | WO 03/092582 | 11/2003 |

OTHER PUBLICATIONS

Azzouz et al., "Lentiviral vectors for treating and modeling human CNS disorders", *J Gene Med*, 6(9), 951-962 (2004).

Burton et al., "Gene therapy progress and prospects: Parkinson's disease", *Gene Ther*, 10(20), 1721-1727 (2003).

Hsich et al., "Critical issues in gene therapy for neurologic disease", *Hum Gene Ther*, 13(5), 579-604 (2002).

Rainov et al., "Clinical trials with retrovirus mediated gene therapy—what have we learned?", *J Neurooncol*, 65(3), 227-236 (2003).

Verma et al., "Gene therapy—promises, problems and prospects", *Nature*, 389(6648), 239-242 (1997).

International Search Report from PCT application serial No. PCT/US2004/39076, mailed Apr. 20, 2005.

Besnard et al., "Multiple interacting sites regulate astrocyte-specific transcription of the human gene for glial fibrillary acidic protein", *J Biol Chem*, 266(28), 18877-18883 (1991).

Blömer et al., "Highly efficient and sustained gene transfer in adult neurons with a lentivirus vector", *J Virol*, 71(9), 6641-6649 (1997).

Brooks et al., "Functional correction of established central nervous system deficits in an animal model of lysosomal storage disease with feline immunodeficiency virus-based vectors", *PNAS*, 99(9), 6216-6221 (2002).

Dylla et al., "Improved apical airway epithelia targeting properties of FIV vector pseudotyped with envelopes from LCMV", *Molecular Therapy*, 9, Supplement 1, p. S186, abstract 491, (2004).

Loewen et al., "Transgene-specific toxicity in lentiviral vector-transduced feline TM in vivo", *ARVO Annual Meeting Abstract Search and Program Planner*, abstract 1147, Annual Meeting of the Association for Research in Vision and Opthalmology, Fort Lauderdale, FL, USA, May 4-8, 2003 (2003).

Petreanu et al., "Maturation and death of adult-born olfactory bulb granule neurons: Role of olfaction", *J Neurosci*, 22(14), 6106-6113 (2002).

Sinnayah et al., "Targeted viral delivery of Cre recombinase induces conditional gene deletion in cardiovascular circuits of the mouse brain", *Physiol Genomics*, 18(1), 25-32 (2004).

(Continued)

*Primary Examiner*—David Guzo
(74) *Attorney, Agent, or Firm*—Viksnins Harris & Padys PLLP

(57) ABSTRACT

The present invention provides novel pseudotyped retroviral vectors that can transduce human and other cells. Vectors are provided that are packaged efficiently in packaging cells and cell lines to generate high titer recombinant virus stocks expressing novel envelope glycoproteins. The present invention further relates to compositions for gene therapy.

5 Claims, 3 Drawing Sheets

OTHER PUBLICATIONS

Stein et al., "Gene transfer to the brain using feline immunodeficiency virus-based lentivirus vectors", *Methods Enzymol*, 346, 433-454 (2002).

Stein et al., "The lymphocytic choriomeningitis virus envelope glycoprotein targets lentiviral gene transfer vector to neural progenitors in the murine brain", *Mol Ther*, 11(3), 382-389 (2005).

Wichterle et al., "Direct evidence for homotypic, glia-independent neuronal migration", *Neuron*, 18(5), 779-791 (1997).

Wong et al., "Transduction patterns of pseudotyped lentiviral vectors in the nervous system", *Mol Ther*, 9(1), 101-111 (2004).

GenBank Accession No. V00878 dated Feb. 25, 2003.

Altschul et al., "Gapped BLAST and PSI-BLAST: a new generation of protein database search programs," *Nucl. Acids. Res.*, 1997, 25(17):3389-3402.

Altschul et al., "Basic Local Alignment Search Tool," *J. Mol. Biol.*, 1990, 215:403-410.

Alvarez-Buylla et al., "Identification of neural stem cells in the adult vertebrate brain," *Brain Res. Bull.*, 2002, 57(6):751-758.

Beyer et al., "Oncoretrovirus and Lentivirus Vectors Pseudotyped with Lymphocytic Choriomeningitis Virus Glycoprotein: Generation, Concentration, and Broad Host Range," *J. Virol.*, 2002, 76(3):1488-1495.

Beyer et al., "Recombinant Expression of Lymphocytic Choriomeningitis Virus Strain WE Glycoproteins: a Single Amino Acid Makes the Difference," *J. Virol.*, 2001, 75(2):1061-1064.

Boshart et al., "A Very Strong Enhancer Is Located Upstream of an Immediate Early Gene of Human Cytomegalovirus," *Cell*, 1985, 41:521-530.

Buchmeier et al., "Arenaviridae: The Viruses and Their Replication," *Fields Virology*, 4th ed., 2001, Knipe and Howley (eds.), Lippincott Williams & Wilkins, vol. 2, pp. 1635-1668.

Burns et al., "Vesicular stomatitis virus G glycoprotein pseudotyped retroviral vectors: Concentration to very high titer and efficient gene transfer into mammalian and nonmammalian cells," *Proc. Natl. Acad. Sci. USA*, 1993, 90:8033-8037.

Cao et al., "Identification of α-Dystroglycan as a Receptor for Lymphocytic Choriomeningitis Virus and Lassa Fever Virus," *Science*, 1998, 282:2079-2081.

Chang et al., "Human Immunodeficiency Viruses Containing Heterologous Enhancer/Promoters Are Replication Competent and Exhibit Different Lymphocyte Tropisms," *J. Virol.*, 1993, 67:743-752.

Chen et al., "Generation of packaging cell lines for pseudotyped retroviral vectors of the G protein of vesicular stomatitis virus by using a modified tetracycline inducible system," *Proc. Natl. Acad. Sci. USA*, 1996, 93:10057-10062.

Corpet et al., "Multiple sequence alignment with hierarchical clustering," *Nucl. Acids. Res.*, 1988, 16:10881-10891.

Culver et al., "Lymphocyte Gene Therapy," *Human Gene Ther.*, 1991, 2(2):107-109.

DePolo et al., "VSV-G Pseudotyped Lentiviral Vector Particles Produced in Human Cells Are Inactivated by Human Serum," *Mol. Ther.*, 2000, 2:218-222.

Dijkema et al., "Cloning and expression of the chromosomal immune interferon-gene of the rat," *EMBO J.*, 1985, 4(3):761-767.

Doetsch et al., "Subventricular Zone Astrocytes Are Neural Stem Cells in the Adult Mammalian Brain," *Cell*, 1999, 97(6):703-716.

Doetsch et al., "Regeneration of a germinal layer in the adult mammalian brain," *Proc. Natl. Acad. Sci. USA*, 1999, 96(20):11619-11624.

Duisit et al., "Five Recombinant Simian Immunodeficiency Virus Pseudotypes Lead to Exclusive Transduction of Retinal Pigmented Epithelium in Rat," *Mol. Ther.*, 2002, 6(4):446-454.

Gewirtz, "Oligodeoxynucleotide-Based Therapeutics for Human Leukemias," *Stem Cells*, 1993, 11(Suppl. 3):96-103.

Goff, "Intracellular trafficking of retroviral genomes during the early phase of infection: viral exploitation of cellular pathways," *J. Gene Med.*, 2001, 3:517-528.

Gorman et al., "The Rous sarcoma virus long terminal repeat is a strong promoter when introduced into a variety of eukaryotic cells by DNA-mediated transfection," *Proc. Natl. Acad. Sci. USA*, 1982, 79:6777-6781.

Grossman et al., "Successful ex vivo gene therapy directed to liver in a patient with familiar hypercholesterolaemia," *Nat. Genet.*, 1994, 6:335-341.

Henry and Campbell, "A Role for Dystroglycan in Basement Membrane Assembly," *Cell*, 1998, 95:859-870.

Henry and Campbell, "Dystroglycan inside and out," *Curr. Opin. Cell Biol.*, 1999, 11:602-607.

Higgins and Sharp; "Fast and sensitive multiple sequence alignments on a microcomputer," *CABIOS*, 1989, 5(2):151-153.

Higgins et al, "CLUSTAL: a package for performing multiple sequence alignment on a microcomputer," *Gene*, 1988, 73:237-244.

Huang et al., "Parallelization of a local similarity algorithm," *CABIOS*, 1992, 8(2):155-165.

Johnston et al., "Minimum Requirements for Efficient Transduction of Dividing and Nondividing Cells by Feline Immunodeficiency Virus Vectors," *J. Virol.*, 1999, 73(6):4991-5000.

Kang et al., "In Vivo Gene Transfer Using a Nonprimate Lentiviral Vector Pseudotyped with Ross River Virus Glycoproteins," *J. Virol.*, 2002, 76(18):9378-9388.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Kasid et al., "Human gene transfer: Characterization of human tumor-infiltrating lymphocytes as vehicles for retroviral-mediated gene transfer in man," *Proc. Natl. Acad. Sci. USA*, 1990, 87:473-477.

Kenyon et al., "Aerosol Infection of Rhesus Macaques with Junin Virus," *Intervirology*, 1992, 33:23-31.

Kim et al., "Use of the human elongation factor 1α promoter as a versatile and efficient expression system," *Gene*, 1990, 91:217-223.

Lehninger, "The amino acid building blocks of proteins," *Biochemistry*, 2nd edition, 1975, The Johns Hopkins University School of Medicine, pp. 73-75.

Lever, "HIV and other lentivirus-based vectors," *Gene Therapy*, 1996, 3:470-471.

Maniatis et al., "Regulation of Inducible and Tissue-Specific Gene Expression," *Science*, 1987, 236:1237-1245.

Mann et al., "Construction of a Retrovirus Packaging Mutant and Its Use to Produce Helper-Free Defective Retrovirus," *Cell*, 1983, 33:153-159.

Markowitz et al., "A Safe Packaging Line for Gene Transfer: Separating Viral Genes on Two Different Plasmids," *J. Virol.*, 1988, 62(4):1120-1124.

Meinkoth and Wahl, "Hybridization of Nucleic Acids Immobilized on Solid Supports," *Anal. Biochem.*, 1984, 138:267-284.

Miletic et al., "Retroviral Vectors Pseudotyped with Lymphocytic Choriomeningitis Virus," *J. Virol.*, 1999, 73(7):6114-6116.

Miller, "Human gene therapy comes of age," *Nature*, 1992, 357:455-460.

Miller, "Cell-surface receptors for retroviruses and implications for gene transfer," *Proc. Natl. Acad. Sci. USA*, 1996, 93:11407-11413.

Mizushima and Nagata, "pEF-BOS, a powerful mammalian expression vector," *Nucl. Acids Res.*, 1990, 18(17):5322.

Myers and Miller, "Optimal alignments in linear space," *CABIOS*, 1988, 4(1):11-17.

Neckers and Whitesell, "Antisense technology: biological utility and practical considerations," *Amer. J. Physiol.*, 1993, 265:L1-L12.

Needleman and Wunsch, "A General Method Applicable to the Search for Similarities in the Amino Acid Sequence of Two Proteins," *J. Mol. Biol.*, 1970, 48:443-453.

Park et al., "Therapeutic levels of human factor VIII and IX using HIV-1-based lentiviral vectors in mouse liver," *Blood*, 2000, 96(3):1173-1176.

Pearson and Lipman, "Improved tools for biological sequence comparison," *Proc. Natl. Acad. Sci. USA*, 1988, 85:2444-2448.

Pearson et al., "Using the FASTA Program to Search Protein and DNA Sequence Databases," *Meth. Mol. Biol.*, 1994, 24:307-331.

Rosenberg, "Human Gene Marker/Therapy Clinical Protocols," *Human Gene Therapy*, 1994, 5(1):140.

Russell and Miller, "Foamy Virus Vectors," *J. Virol.*, 1996, 70(1):217-222.

Sandrin et al., "Lentiviral vectors pseudotyped with a modified RD114 envelope glycoprotein show increased stability in sera and augmented transduction of primary lymphocytes and CD34+ cells derived from human and nonhuman primates," *Blood*, 2002, 100(3):823-832.

Schauber et al., "Lentiviral vectors pseudotyped with baculovirus gp64 efficiently transduce mouse cells in vivo and show tropism restriction against hematopoietic cell types in vitro," *Gene Ther.*, 2004, 11:266-275.

Schwartz et al., "Distinct RNA Sequences in the *gag* Region of Human Immunodeficiency Virus Type 1 Decrease RNA Stablity and Inhibit Expression in the Absence of Rev Protein," *J. Virol.*, 1992, 66(1):150-159.

Sinn et al., "Lentivirus Vectors Pseudotyped with Filoviral Envelope Glycoproteins Transduce Airway Epithelia from the Apical Surface Independently of Folate Receptor Alpha," *J. Virol.*, 2003, 77(10):5902-5910.

Smith and Waterman, "Comparison of Biosequences," *Adv. Appl. Math.*, 1981, 2:482-489.

Spiropoulou et al., "New World Arenavirus Clade C, but Not Clade A and B Viruses, Utilizes α-Dystroglycan as Its Major Receptor," *J. Virol.*, 2002, 76(10):5140-5146.

Steffy and Wong-Staal, "Genetic Regulation of Human Immunodeficiency Virus," *Microbiol. Rev.*, 1991, 55:193-205.

Stein et al., "In Vivo Treatment of Hemophilia A and Mucopolysaccharidosis Type VII Using Nonprimate Lentiviral Vectors," *Mol. Ther.*, 2001, 3:850-856.

Stewart et al., "Lentiviral delivery of HIV-1 Vpr protein induces apoptosis in transformed cells," *Proc. Natl. Acad. Sci. USA*, 1999, 96(21):12039-12043.

Stryer, "Conformation and Dynamics," *Biochemistry*, 2nd edition, 1981, W.H. Freeman and Co., San Francisco, pp. 14-15.

Subbramanian and Cohen, "Molecular Biology of the Human Immunodeficiency Virus Accessory Proteins," *J. Virol.*, 1994, 68(11):6831-6835.

Talbott et al., "Nucleotide sequence and genomic organization of feline immunodeficiency virus," *Proc. Natl. Acad. Sci. USA*, 1989, 86:5743-5747.

Trono et al., "HIV Accessory Proteins: Leading Roles for the Supporting Cast," *Cell*, 1995, 82:189-192.

Uetsuki et al., "Isolation and Characterization of the Human Chromosomal Gene for Polypeptide Chain Elongation Factor-1α," *J. Biol. Chem.*, 1989, 264:5791-5798.

Voss et al., "The role of enhancers in the regulation of cell-type-specific transcriptional control," *Trends Biochem. Sci.*, 1986, 11:287-289.

Wang et al., "Feline immunodeficiency virus vectors persistently transduce nondividing airway epithelia and correct the cystic fibrosis defect," *J. Clin. Invest.*, 1999, 104:R55-62.

Watson et al., "Targeted Transduction Patterns in the Mouse Brain by Lentivirus Vectors Pseudotyped with VSV, Ebola, Mokola, LCMV, or MuLV Envelope Proteins," *Mol. Ther.*, 2002, 5(5):528-537.

White et al., "Airway Epithelial Cell Wound Repair Mediated by α-Dystroglycan," *Am. J. Respir. Cell Mol. Biol.*, 2001, 24:179-186.

Yamada et al., "Nanoparticles for the delivery of genes and drugs to human hepatocytes," *Nature Biotechnology*, 2003, 21(8):885-890.

\* cited by examiner

METHODS FOR PRODUCING AND USING IN VIVO PSEUDOTYPED RETROVIRUSES USING ENVELOPE GLYCOPROTEINS FROM LYMPHOCYTIC CHORIOMENINGITIS VIRUS (LCMV)

CROSS-REFERENCE TO RELATED APPLICATIONS

This application is a Continuation application of U.S. application Ser. No. 10/993,319 filed on Nov. 19, 2004, now U.S. Pat. No. 7,160,727, which is a continuation-in-part of U.S. application Ser. No. 10/718,262, filed Nov. 20, 2003, now U.S. Pat. No. 7,135,339.

U.S. GOVERNMENT RIGHTS

Portions of the present invention were made with support of the United States Government via a grant from the National Institutes of Health under grant numbers PPG HL-51670, DK54759, and NS34568. The U.S. Government therefore has certain rights in the invention.

FIELD OF THE INVENTION

The present invention relates to improved pseudotyped retrovirus-derived vectors useful for the expression of genes in eukaryotic cells.

BACKGROUND OF THE INVENTION

Viral vectors transduce genes into target cells with high efficiencies owing to specific virus envelope-host cell receptor interaction and viral mechanisms for gene expression. Consequently, viral vectors have been used as vehicles for the transfer of genes into many different cell types. The ability to introduce and express a foreign gene in a cell is useful for the study of gene expression and the elucidation of cell lineages. Retroviral vectors, capable of integration into the cellular chromosome, have also been used for the identification of developmentally important genes via insertional mutagenesis. Viral vectors, and retroviral vectors in particular, are also used in therapeutic applications (e.g., gene therapy), in which a gene (or genes) is added to a cell to replace a missing or defective gene due to an inherited or acquired condition or to inactivate a pathogen such as a virus.

In view of the wide variety of potential genes available for therapy, it is clear that an efficient means of delivering these genes is needed in order treat infectious, as well as non-infectious diseases. Factors affecting viral vector usage include tissue tropism, stability of virus preparations, genome packaging capacity, and construct-dependent vector stability. In addition, in vivo application of viral vectors is often limited by host immune responses against viral structural proteins and/or transduced gene products.

Lymphocytic choriomeningitis virus was the first member of the arenavirus family identified, originally isolated in a sample from an outbreak of St. Louis encephalitis in 1933 (Buchmeier et al., "Arenaviridae: The Viruses and Their Replication." In: Knipe D M, Howley P M, eds. *Fields Virology.* 4th ed. Philadelphia: Lippincott Williams & Wilkins, 2001: 1635-1668). The virus is endemic in rodents, which serve as a reservoir. LCMV is generally noncytopathic and the most common human disease associated with LCMV is aseptic meningitis. A characteristic feature of infection with wild type LCMV is widespread infection of epithelial tissues (Buchmeier et al., supra). Of interest, there is evidence to suggest that LCMV may be spread by inhalation of infected material [Kenyon et al., *Intervirology*, 33:23-31 (1992)].

SUMMARY OF THE INVENTION

The present invention provides a pseudotyped retrovirus virion containing an envelope glycoprotein from Lymphocytic Choriomeningitis Virus (LCMV) strain WE54 (LCMV-WE54). LCMV-WE54 is also called LCMV-HPI in the literature. The pseudotyped retrovirus virion may contain an LCMV-WE54 envelope glycoprotein that is the same as wild type LCMV-WE54, or it may contain a variant LCMV envelope glycoprotein. A variant LCMV envelope glycoprotein that is the same as wild type LCMV-WE54 envelope glycoprotein except for containing slight variations in the amino acid sequence of the protein. For example, one variant LCMV-WE54 variant has an amino acid sequence identical to the wild type protein sequence except that it contains a phenylalanine (F) at position/residue 260 instead of a leucine (L). In another embodiment, the LCMV-WE54 protein contains a phenylalanine (F) at position/residue rather than a serine (S). Further, the LCMV envelope glycoprotein may have both a phenylalanine at position 260 and at position 153, i.e., LCMV-L260F/S153F. The invention also provides further provides polynucleotide vectors that contain polynucleotides encoding an LCMV-WE54 envelope glycoprotein. The virions and vectors provided herein can be delivered to target cells such as nervous system cells, for example.

In one aspect, the invention thus features a method for transducing a nervous system cell with a transgene. The method can include contacting the cell with a pseudotyped retrovirus virion containing an LCMV strain WE-54 envelope glycoprotein and the transgene. The envelope glycoprotein can have a phenylalanine at residue 260, a phenylalanine at residue 153, or a phenylalanine at residue 260 and a phenylalanine at residue 153. The retrovirus virion can be a lentivirus virion (e.g., a feline immunodeficiency virus virion).

In another aspect, the invention features a method for transducing a nervous system cell with a transgene, wherein the method includes contacting the neural cell with a vector containing (a) a nucleic acid encoding an envelope glycoprotein from LCMV strain WE-54, and (b) the transgene. The envelope glycoprotein can have a phenylalanine at residue 260, a phenylalanine at residue 153, or a phenylalanine at residue 260 and a phenylalanine at residue 153.

In another aspect, the invention features a method for treating a mammal diagnosed with a neurogenetic disorder. The method can include administering to the mammal a pseudotyped retrovirus virion containing (a) an LCMV strain WE-54 envelope glycoprotein, and (b) a transgene. The neurogenetic disorder can be a lysosomal storage disease, Huntington's disease, Parkinson's disease, amyotrophic lateral sclerosis, an ataxia, dentatorubral-pallidoluysian atrophy, prion disease, or Alzheimer's disease. The envelope glycoprotein can have a phenylalanine at residue 260, a phenylalanine at residue 153, or a phenylalanine at residue 260 and a phenylalanine at residue 153.

The invention also provides a pseudotyped feline immunodeficiency virus (FIV) virion comprising a envelope glycoprotein from LCMV envelope glycoprotein, such as LCMV-WE54. The envelope glycoprotein may be a variant of the wild type LCMV.

The present invention further provides an isolated polynucleotide vector containing a polynucleotide encoding an LCMV-WE54 envelope glycoprotein. The polynucleotide may encode the wild type LCMV-WE54 envelope glycoprotein, or it may encode a variant LCMV envelope glycoprotein as described above.

The present invention also provides a method of producing in the form of infectious particles a transgene vector containing a remedial gene, by transfecting a cell with (a) a packaging vector; (b) a vector containing a nucleic acid encoding a wild type or variant LCMV envelope glycoprotein, and (c) a transgene vector containing the remedial gene and a functional packaging signal, which by itself is incapable of causing a cell to produce transducing vector particles, wherein the cell produces infectious transducing vector particles containing the transducing transgene vector in RNA form, a Gag protein, a Pol protein, and a pseudotyped envelope glycoprotein. The packaging may be inducible.

The present invention also provides a method of delivering a remedial gene to a target cell in vivo, comprising producing viral particles by the method described above, and then infecting the target cell with an effective amount of the infectious transgene vector particles. The target cell may be an airway epithelial cell, a central nervous system cell, or a hepatocyte cell.

The present invention also provides a packaging cell containing a nucleic acid encoding a pseudotyping LCMV envelope glycoprotein. In one embodiment the packaging cell stably expresses a wild type LCMV-WE54. In another embodiment, the packaging cell stably expresses a variant envelope glycoprotein from LCMV envelope glycoprotein, containing a phenylalanine at residue 260 and/or a phenylalanine at residue 153. Such packaging cells of the present invention may further contain a transgene vector, and the transgene vector may contain a remedial gene.

The present invention provides a method involving inserting a wild type or variant LCMV envelope glycoprotein into a lipid vesicle, and electroporating plasmid DNA into the lipid vesicle. See, for example, Yamada et al., *Nature Biotech.* 21:885-890 (2003).

The present invention also provides a packaging cell containing a nucleic acid encoding a pseudotyping LCMV envelope glycoprotein. In one embodiment the packaging cell stably expresses a wild type LCMV-WE54. In another embodiment, the packaging cell stably expresses a variant envelope glycoprotein from LCMV envelope glycoprotein, containing a phenylalanine at residue 260 and/or a phenylalanine at residue 153. Such packaging cells of the present invention may further contain a transgene vector, and the transgene vector may contain a remedial gene. The present invention provides a packaging cell line containing an inducible expression sequence that encodes a wild type or variant LCMV envelope glycoprotein.

The present invention also provides a method of producing in the form of infectious particles a transducing gene transfer vector containing a remedial gene, by transfecting a packaging cell as described above with a packaging vector, and a transgene vector containing the remedial gene and a functional packaging signal, which by itself is incapable of causing a cell to produce transducing transgene vector particles, wherein the cell produces infectious transducing vector particles containing the transducing transgene vector in RNA form, a Gag protein, a Pol protein, pseudotyped with an envelope glycoprotein.

The present invention further provides a kit containing a vector containing a nucleic acid encoding a wild type or variant LCMV envelope glycoprotein; and a transgene vector containing a functional and compatible packaging signal, the transgene vector being incapable by itself of causing a cell transfected by the transgene vector to encapsulate the RNA form of the transgene vector into a retroviral particle containing a baculovirus envelope protein.

In one embodiment, the present invention provides a method of treating an airway epithelial cell, wherein the airway epithelial cell has an apical surface and a basolateral surface, by administering to the apical surface of the airway epithelial cell a Lymphocytic Choriomeningitis Virus (LCMV) strain WE-54 pseudotyped vector. In one embodiment, the airway epithelial cell is a human airway epithelial cell.

"Polypeptides" and "protein" are used interchangeably to refer to polymers of amino acids and do not refer to any specific lengths. These terms also include post-translationally modified proteins, for example glycosylated, acetylated, phosphorylated proteins and the like. Also included within the definition are, for example, proteins containing one or more analogs of an amino acid (including, for example, unnatural amino acids), proteins with substituted linkages, as well as other modifications known in the art, both naturally occurring and non-naturally occurring. Envelope peptides or polypeptides comprise at least about 2, 3, 5, 10, 15, 20, 25, 30, or 50 or more consecutive amino acid residues.

"Isolated" DNA, RNA, peptides, polypeptides, or proteins are DNA, RNA, peptides polypeptides or proteins that are isolated or purified relative to other DNA, RNA, peptides, polypeptides, or proteins in the source material. For example, "isolated DNA" encoding the envelope protein (which would include cDNA) refers to DNA purified relative to DNA that encodes polypeptides other than the envelope protein.

The numbering of amino acid positions within the LCMV envelope glycoprotein of the WE54 strain is according to the numbering of GenBank Accession No. AJ318512 (designated WE-HPI). Thus, position 260 is relative to the methionine at the first position of the sequence set forth in GenBank Accession No. AJ318512.

"Pharmaceutically acceptable" refers to molecular entities and compositions that are physiologically tolerated and do not typically produce an allergic or toxic reaction, such as gastric upset, dizziness and the like when administered to a subject or a patient. Exemplary subjects of the invention are vertebrates, mammals, and humans.

"Agent" herein refers to any chemical substance that causes a change. For example, agents include, but are not limited to, therapeutic genes, proteins, drugs, dyes, toxins, pharmaceutical compositions, labels, radioactive compounds, probes etc.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1. LCMV WE54-FIV (n=13) transduces polarized airway epithelia predominantly from the apical surface while VSVG (n=5) enters better from the basolateral surface. Vectors were applied to the apical or basolateral surfaces and gene transfer measured after 4 days. This contrasts with the findings from the VSVG envelope (Wang et al., *J. Clin. Invest.* 104(11):R55-62 (1999)).

FIG. 2. Pseudotyping FIV with the LCMV-WE54 L260F mutant confers enhanced tropism human airway epithelial gene transfer. FIV expressing beta-gal transgene was used. Enzyme activity measured by galactolight assay 4 days post-transduction.

Figure 3:
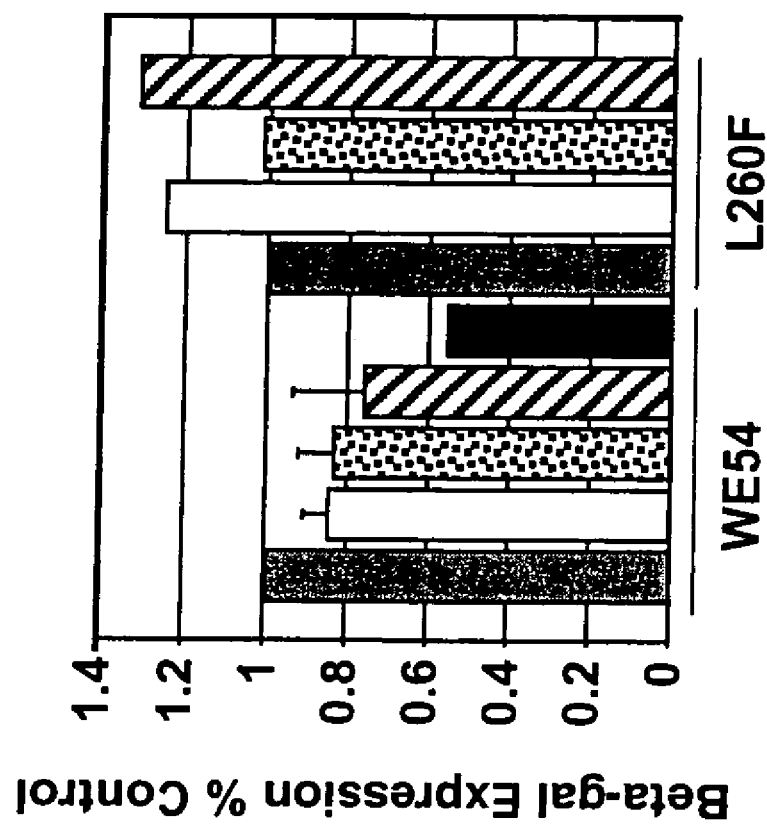
FIG. 3. Effects of blocking agents on LCMV-FIV pseudotyped with WE54 or L260F envs. Blue bars represent control levels of beta gal in absence of inhibitors. White bars and grey bars are laminin at 100 or 50 μg/ml, respectively. Hatched bars are IIH6 antibody. Black bar is media containing alpha DG. n=2-3.

DETAILED DESCRIPTION OF THE INVENTION

Retroviruses; Retroviral Vectors

The term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules that encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. There are several genera included within the family Retroviridae, including Cistemavirus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

Retroviruses, including human foamy virus (HFV) and human immunodeficiency virus (HIV) have gained much recent attention, as their target cells are not limited to dividing cells and their restricted host cell tropism can be readily expanded via pseudotyping with vesicular stomatitis virus G (VSV-G) envelope glycoproteins [see, e.g., Burns et al., *Proc. Natl. Acad. Sci. USA* 90:8033-8037 (1993); Lever, *Gene Therapy* 3:470-471 (1996); and Russell and Miller, *J. Virol.,* 70:217-222 (1996)].

Vector systems generally have a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly [Markowitz et al., *J. Virol.,* 62:1120 (1988)]. In one embodiment of the present invention, an FIV system employing a 3-plasmid transfection production method in 293T cells was used [Johnston et al., *J. Virol.* 73:4991-5000 (1999)]. Replication incompetent virus was successfully produced.

The vector DNA is introduced into the packaging cell by any of a variety of techniques (e.g., calcium phosphate coprecipitation, lipofection, electroporation). The viral proteins produced by the packaging cell mediate the insertion of the vector sequences in the form of RNA into viral particles, which are shed into the culture supernatant.

A major limitation in the use of many commonly used retroviral vectors in gene transfer is that many of the vectors are restricted to dividing cells. If a non-dividing cell is the target cell, then a lentivirus, which is capable of infecting non-dividing cells are provided. Alternatively, for cells that are naturally dividing or stimulated to divide by growth factors, murine leukemia virus (MLV) vectors are suitable delivery systems.

In addition to simple retroviruses like MLV, lentiviruses can also be used as the vector. As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, that causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

Lentiviruses including HIV, SIV, FIV and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated, by the expression of Tat through interaction with an RNA target (TAR) in the LTR. Expression of the full-length and spliced mRNAs is then regulated by the function of Rev, which interacts with RNA elements present in the gag region and in the env region (RRE) [Schwartz et al., *J. Virol.,* 66:150-159 (1992)]. Nuclear export of gag-pol and env mRNAs is dependent on the Rev function. In addition to these two essential regulatory genes, a list of accessory genes, including vif, vpr, vpx, vpu, and nef, are also present in the viral genome and their effects on efficient virus production and infectivity have been demonstrated, although they are not absolutely required for virus replication [Wong-Staal and Wong-Staal, *Microbiol. Rev.,* 55:193-205 (1991); Subbramanian and Cohen, *J. Virol.* 68:6831-6835 (1994); and Trono, Cell 82:189-192 (1995)]. A detailed description of the structure of an exemplary lentivirus, HIV-1, is given in U.S. Pat. No. 6,531,123.

A "source" or "original" retrovirus is a wild-type retrovirus from which a pseudotyped retrovirus is derived, or is used as a starting point, during construction of the packaging or transgene vector, for the preparation of one or more of the genetic elements of the vector. The genetic element may be employed unchanged, or it may be mutated (but not beyond the point where it lacks a statistically significant sequence similarity to the original element). A vector may have more than one source retrovirus, and the different source retroviruses may be, e.g., MLV, FIV, HIV-1 and HIV-2, or HIV and SIV. The term "genetic element" includes but is not limited to a gene.

A cognate retrovirus is the wild-type retrovirus with which the vector in question has the greatest percentage sequence identity at the nucleic acid level. Normally, this will be the same as the source retrovirus. However, if a source retrovirus is extensively mutated, it is conceivable that the vector will then more closely resemble some other retrovirus. It is not necessary that the cognate retrovirus be the physical starting point for the construction; one may choose to synthesize a genetic element, especially a mutant element, directly, rather than to first obtain the original element and then modify it. The term "cognate" may similarly be applied to a protein, gene, or genetic element (e.g., splice donor site or packaging signal). When referring to a cognate protein, percentage sequence identities are determined at the amino acid level.

The term "cognate" retrovirus may be difficult to interpret in the extreme case, i.e., if all retroviral genetic elements have been replaced with surrogate non-lentiviral genetic elements. In this case, the source retrovirus strain mentioned previously is arbitrarily considered to be the cognate retrovirus.

The term "replication" as used herein in reference to a virus or vector, refers not to the normal replication of proviral DNA in a chromosome as a consequence of cell reproduction, or the autonomous replication of a plasmid DNA as a result of the presence of a functional origin of replication. Instead "replication" refers to the completion of a complete viral life cycle, wherein infectious viral particles containing viral RNA enter a cell, the RNA is reverse transcribed into DNA, the DNA integrates into the host chromosome as a provirus, the infected cell produces virion proteins and assembles them with full length viral genomic RNA into new, equally infectious particles.

The term "replication-competent" refers to a wild-type virus or mutant virus that is capable of replication, such that replication of the virus in an infected cell result in the production of infectious virions that, after infecting another, previously uninfected cell, causes the latter cell to likewise produce such infectious virions. The present invention contemplates the use of replication-defective virus.

As used herein, the term "attenuated virus" refers to any virus (e.g., an attenuated lentivirus) that has been modified so that its pathogenicity in the intended subject is substantially reduced. The virus may be attenuated to the point it is non-pathogenic from a clinical standpoint, i.e., that subjects exposed to the virus do not exhibit a statistically significant increased level of pathology relative to control subjects.

The present invention contemplates the preparation and use of a modified retrovirus. In some embodiments, the retrovirus is an mutant of murine leukemia virus, human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus, or a virus comprised of portions of more than one retroviral species (e.g., a hybrid, comprised of portions of MLV, FIV, HIV-1 and HIV-2, or HIV- and/or SIV).

A reference virus is a virus whose genome is used in describing the components of a mutant virus. For example, a particular genetic element of the mutant virus may be said to differ from the cognate element of the reference virus by various substitutions, deletions or insertions. It is not necessary that the mutant virus actually be derived from the reference virus.

The preferred reference FIV sequence is found in Talbott et al., *Proc. Natl. Acad. Sci. USA*, 86:5743-7 (1989); GenBank Accession No. NC_001482. In certain embodiments, a three-plasmid transient transfection method can be used to produce replication incompetent pseudotyped retroviruses (e.g., FIV). General methods are described in Wang et al., *J. Clin. Invest.* 104:R55-62 (1999); and Johnston et al., *J. Virol.* 73:4991-5000 (1999).

Retroviral Vector System

The present invention contemplates a retroviral gene amplification and transfer system comprising a transgene vector, one or more compatible packaging vectors, an envelope vector, and a suitable host cell. The vectors used may be derived from a retrovirus (e.g., a lentivirus). Retrovirus vectors allow (1) transfection of the packaging vectors and envelope vectors into the host cell to form a packaging cell line that produces essentially packaging-vector-RNA-free viral particles, (2) transfection of the transgene vector into the packaging cell line, (3) the packaging of the transgene vector RNA by the packaging cell line into infectious viral particles, and (4) the administration of the particles to target cells so that such cells are transduced and subsequently express a transgene.

Either the particles are administered directly to the subject, in vivo, or the subject's cells are removed, infected in vitro with the particles, and returned to the body of the subject.

The packaging vectors and transgene vectors of the present invention will generate replication-incompetent viruses. The vectors chosen for incorporation into a given vector system of the present invention are such that it is not possible, without further mutation of the packaging vector(s) or transgene vector, for the cotransfected cells to generate a replication-competent virus by homologous recombination of the packaging vector(s) and transgene vector alone. The envelope protein used in the present system can be a retroviral envelope, a synthetic or chimeric envelope, or the envelope from a non-retroviral enveloped virus (e.g., baculovirus).

Packaging Signal

As used herein, the term "packaging signal" or "packaging sequence" refers to sequences located within the retroviral genome or a vector that are required for, or at least facilitate, insertion of the viral or vector RNA into the viral capsid or particle. The packaging signals in an RNA identify that RNA as one that is to be packaged into a virion. The term "packaging signal" is also used for convenience to refer to a vector DNA sequence that is transcribed into a functional packaging signal. Certain packaging signals may be part of a gene, but are recognized in the form of RNA, rather than as a peptide moiety of the encoded protein.

The key distinction between a packaging vector and a transgene vector is that in the packaging vector, the major packaging signal is inactivated, and, in the transgene vector, the major packaging signal is functional. Ideally, in the packaging vector, all packaging signals would be inactivated, and, in the transgene vector, all packaging signals would be functional, However, countervailing considerations, such as maximizing viral titer, or inhibiting homologous recombination, may lend such constructs less desirable.

Packaging System; Packaging Vectors; Packaging Cell Line

A packaging system is a vector, or a plurality of vectors, which collectively provide in expressible form all of the genetic information required to produce a virion that can encapsidate suitable RNA, transport it from the virion-producing cell, transmit it to a target cell, and, in the target cell, cause the RNA to be reverse transcribed and integrated into the host genome in a such a manner that a transgene incorporated into the aforementioned RNA can be expressed. However, the packaging system must be substantially incapable of packaging itself. Rather, it packages a separate transgene vector.

In the present invention, the packaging vector will provide functional equivalents of the gag and pol genes (a "GP" vector). The env gene(s) will be provided by the envelope vector. In theory, a three vector system ("G", "P", and "E" vectors) is possible if one is willing to construct distinct gag and pol genes on separate vectors, and operably link them to different regulatable promoters (or one to a regulatable and the other to a constitutive promoter) such that their relative levels of expression can be adjusted appropriately.

A packaging cell line is a suitable host cell transfected by a packaging system that, under achievable conditions, produces viral particles. As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi$^+$ sequence (designated as Δ-psi), and a 5'-LTR-env-3'-LTR fragment that is also Δ-psi located at another chromosomal site. While both of these segments are transcribed constitutively, because the psi$^+$ region is missing and the viral RNA molecules produced are less than full-size, empty viral particles are formed.

If a host cell is transfected by the packaging vector(s) alone, it produces substantially only viral particles without the full-length packaging vector. In one example, less than 10% of the viral particles produced by the packaging cell contain full length packaging vector-derived RNA. However, since the packaging vector lacks a functional primer binding site, even if these particles infect a new cell, the packaging vector RNA will not be reverse transcribed back into DNA and therefore the new cell will not produce virion. Thus, by itself, the packaging vector is a replication-incompetent virus.

In some embodiments, the packaging cell and/or cell line contains a transgene vector. The packaging cell line will package the transgene vector into infectious particles. Such a cell line is referred to herein as a "transgenic virion production cell line."

It is contemplated that packaging may be inducible, as well as non-inducible. In inducible packaging cells and packaging cell lines, retroviral particles are produced in response to at least one inducer. In non-inducible packaging cell lines and packaging cells, no inducer is required in order for retroviral particle production to occur.

The packaging vectors necessarily differ from wild-type, replication-competent retroviral genomes by virtue of the inactivation of at least one packaging signal of the cognate wild-type genome. More than one packaging signal may be inactivated. In one example, only the retroviral genes provided by the packaging vector are those encoding structural, or essential regulatory, proteins.

Envelope Protein Vectors

The envelope proteins encoded by the packaging vector are viral proteins. The vector containing an envelope protein that is different from the packaging virus genes is commonly referred to as an envelope pseudotyping vector.

Env glycoproteins: The Env glycoproteins of a retrovirus may be replaced with Env glycoproteins of other retroviruses, of non-retroviral viruses, or with chimeras of these glycoproteins with other peptides or proteins. An example of a non-lentiviral envelope glycoprotein of interest is the lymphocytic choriomeningitis virus (LCMV) strain WE54 envelope glycoprotein. These envelope glycoproteins increase the range of cells that can be transduced with retroviral derived vectors. In one example of the present invention, the envelope protein is a "mutant" or variant LCMV-WE54 protein, such as a LCMV envelope glycoprotein containing a single point mutation (L260F). In another embodiment, the variant LCMV envelope glycoprotein contains a single point mutation (S153F). In another embodiment, the variant LCMV envelope glycoprotein contains two point mutations L260F and S153. Such mutations allow further specificity as to what cell types the pseudotyped virus will infect, i.e., the affinity of the vector is modified.

As used herein, the LCMV-WE54 envelope glycoproteins include variants or biologically active fragments of the proteins. A "variant" of the protein is a protein that is not completely identical to a native protein. A variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cysteine, tyrosine, asparagine and glutamine having uncharged polar side chains; aspartate and glutamate having acidic side chains; and lysine, arginine, and histidine having basic side chains (Stryer, *Biochemistry* ($2^{nd}$ ed.), W. H. Freeman and Co., San Francisco (1981) pp. 14-15; Lehninger, *Biochemistry* ($2^{nd}$ ed.), Institute of Electrical & Electronics Engineer (1975), pp. 73-75).

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. One can use the hydropathic index of amino acids in conferring interactive biological function on a polypeptide, wherein it is found that certain amino acids may be substituted for other amino acids having similar hydropathic indices and still retain a similar biological activity.

A variant of the invention may include amino acid residues not present in the corresponding native protein, or may include deletions relative to the corresponding native protein. A variant may also be a truncated fragment as compared to the corresponding native protein, i.e., only a portion of a full-length protein. Protein variants also include peptides having at least one D-amino acid.

The LCMV-WE54 envelope glycoprotein of the present invention may be expressed from isolated nucleic acid (DNA or RNA) sequences encoding the proteins. Amino acid changes from the native to the variant protein may be achieved by changing the codons of the corresponding nucleic acid sequence. Recombinant is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The starting material (such as a gene encoding an LCMV-WE54 envelope glycoprotein) used to make the complexes of the present invention may be substantially identical to wild-type genes, or may be variants of the wild-type gene. Further, the polypeptide encoded by the starting material may be substantially identical to that encoded by the wild-type gene, or may be a variant of the wild-type gene. The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, J. Mol. Biol., 48:443-453 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al, CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., J. Mol. Biol., 215:403 (1990); Nucl. Acids Res., 25:3389 (1990), are based on the algorithm of Karlin and Altschul supra.

Software for performing BLAST analyses is publicly available through the National Center for Biotechnology Information (World Wide Web at "ncbi" dot "nlm" dot "nih" dot "gov"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., Nucl. Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See World Wide Web at "ncbi" dot "nlm" dot "nih" dot "gov." Alignment may also be performed manually by inspection.

For purposes of the present invention, comparison of nucleotide sequences for determination of percent sequence identity to the promoter sequences disclosed herein is made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5°/ C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.*, 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Bind(s) substantially refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes [see, Sambrook et al., *Molecular Cloning: A Laboratory Manual* (3rd ed.), Cold Spring Harbor Laboratory Press, (2001) for a description of SSC buffer]. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Chimeric Env Glycoproteins: A chimera may be constructed of an env glycoprotein and of a ligand that binds to a specific cell Surface receptor in order to target the vector to cells expressing that receptor. Examples are chimeras including FLA16 (a 6 amino acid peptide that binds integrin receptors), erythropoietin (which binds the erythropoietin receptor), human heregulin (which binds the EGF and related receptors). Alternatively, the chimera could include an antibody variable light or heavy domain, or both domains joined by suitable peptide linker (a so-called single chain antibody). Such an antibody domain could target any desired cell surface molecule, such as a tumor antigen, the human low-density lipoprotein receptor, or a determinant on human MHC Class I molecules.

Derivatized Env Glycoproteins: Virions may be chemically, enzymatically or physically modified after production in order to alter their cell specificity. Examples of modifications include chemical or enzymatic addition of a ligand which would be recognized by a cell surface receptor (e.g., addition of lactose so that the virions will transduce human hepatoma cells which express asialoglycoprotein receptors), or incubation of the virus with a biotinylated antibody directed against the vector's Env protein, followed by addition of a streptavidin-linked ligand recognized by the cell-surface receptor. A heterobispecific antibody also could be used to link the virion's Env protein to such a ligand.

Transgene Vectors

A transgene vector is an expression vector that bears an expressible nonretroviral gene of interest and includes at least one functional retroviral packaging signal, so that, after the transgene vector is transfected into a packaging cell line, the transgene vector is transcribed into RNA, and this RNA is packaged into an infectious viral particle. These particles, in turn, infect target cells, their RNA is reverse transcribed into DNA, and the DNA is incorporated into the host cell genome as a proviral element, thereby transmitting the gene of interest to the target cells.

As used herein, the term "transduction" refers to the delivery of a gene(s) using a viral or retroviral vector by means of infection rather than by transfection. In certain embodiments, retroviral vectors are transduced. Thus, a "transduced gene" is a gene that has been introduced into the cell via retroviral or vector infection and provirus integration. In certain embodiments, viral vectors (e.g., "transgene vectors") transduce genes into "target cells" or host cells. The, present invention encompasses transgene vectors that are suitable for use in the present invention that are linked to any gene of interest (or a "marker gene" or "reporter gene," used to indicate infection or expression of a gene).

As used herein, the term "long-term transduction" refers to vectors that are capable of remaining transduced in host or target cells for time periods that are longer than those observed with other vectors. For example, the present invention provides retroviral vectors that are capable of remaining transduced for at least 120 days, at least one year, or for the life of the subject or the necessary time course of treatment. The duration of expression is a function of the choice of promoter and the target cell type, more so than the choice of vector.

The term "stable transduction" or "stably transduced" refers to the introduction and integration of foreign DNA into the genome of the transducted cell. The term "stable transductant" refers to a cell that has stably integrated foreign DNA into the genomic DNA.

The term "transient transduction" or "transiently transduced" refers to the introduction of foreign DNA into a cell where the foreign DNA fails to integrate into the genome of the transducted cell. The foreign DNA persists in the nucleus of the transducted cell for several days. During this time the foreign DNA is subject to the regulatory controls that govern the expression of endogenous genes in the chromosomes. The term "transient transductant" refers to cells that have taken up foreign DNA but have failed to integrate this DNA.

In some embodiments, the target and/or host cells of the present invention are "non-dividing" cells. These cells include cells such as neuronal cells that do not normally divide. However, it is not intended that the present invention be limited to non-dividing cells (including, but not limited to muscle cells, white blood cells, spleen cells, liver cells, eye cells, epithelial cells).

In some embodiments, the vector and the vector progeny are capable of transducing a plurality of target cells so as to achieve vector titers of at least $10^5$ cfu/ml. The multiplicity of infection (MOI) may be at least one (i.e., one hit on average per cell), or even at least two.

Transgene

The transgene is a gene encoding a polypeptide that is foreign to the retrovirus(es) from which the vector is primarily derived, and has a useful biological activity in the organism that is ultimately infected with the transgene vector in its virion-packaged form.

The transgene may be identical to a wild-type gene, or it may contain one or more mutations. The transgene may be derived from genomic DNA, cDNA, synthetic DNA, or a combination thereof. Intronless "minigenes," which are normal genes from which introns have been removed, have been especially popular. Intron-containing genes may be employed, but they may be inserted into the vector in the reverse orientation if removal of the introns is not desired. Silent mutations may be introduced to facilitate gene manipulation, to avoid undesirable secondary structure in the mRNA, to inhibit recombination, to control splicing, etc. Non-silent mutations alter the encoded protein, and may be either gratuitous, or aimed at beneficially altering the biological activity of the protein.

One example of a transgene is a remedial gene. As used herein, the term "remedial gene" refers to a gene whose expression is desired in a cell to correct an error in cellular metabolism, to inactivate a pathogen or to kill a cancerous cell. For example, the adenosine deaminase (ADA) gene is the remedial gene when carried on a retroviral vector used to correct ADA deficiency in a patient.

The applications of transgenes include the following:

cell marking: for some purposes, it is useful to follow cells after they have been introduced into a patient.

anti-pathogen or anti-parasite: anti-pathogen genes or anti-parasite can be introduced into a host infested, or especially vulnerable to infestation, by the pathogen or parasite in question.

genetic disease: an inherited genetic defect may be ameliorated by supplying a functional gene.

It is not necessary that the endogenous gene be repaired by homologous recombination. Monogenetic genetic diseases are of particular interest. Suitable approaches include providing genes encoding the enzyme ADA, especially to hematopoietic stem cells so as to provide long term treatment of ADA deficiency; and correcting familial hypercholesterolemia with a vector encoding the low density lipoprotein (LDL) receptor.

Gene therapy has been used to successfully correct inborn errors of metabolism using existing vector systems. For example, the adenosine deaminase gene has been introduced into peripheral blood lymphocytes and cord blood stem cells via retroviral vectors in order to treat patients with severe combined immunodeficiency due to a lack of functional adenosine deaminase [Culver et al., Human Gene Ther., 2:107 (1991)]. Partial correction of familial hypercholesterolemia has been achieved using existing retroviral vectors to transfer the receptor for low density lipoproteins (LDL) into hepatocytes. However, it was estimated that only 5% of the liver cells exposed to the recombinant virus incorporated the LDL receptor gene with the vector utilized [Grossman et al., Nat. Genet., 6:335 (1994)].

A number of single-gene disorders have been targeted for correction using gene therapy. These disorders include hemophilia (lack of Factor VIII or Factor IX), cystic fibrosis (lack of cystic fibrosis transmembrane conductance regulator), emphysema (defective α-1-antitrypsin), thalassemia and sickle cell anemia (defective synthesis of β-globin), phenylketonuria (deficient phenylalanine hydroxylase) and muscular dystrophy (defective dystrophin) [for review see Miller, Nature 357:455 (1992)]. Human gene transfer trials have been approved for a number of these diseases.

The molecular genetics of cystic fibrosis (CF) has been studied and gradually understood in recent years. Many CF patients carry a single amino acid deletion ((F508) mutation in one of the two nucleotide-binding domains in the CF transmembrane regulator (CFTR) protein. Other forms of genetic mutations in the CFTR genes have also been identified. This rich genetic information makes CF an ideal gene therapy candidate.

The target cells for CF patients are undifferentiated, proliferating and differentiated, non-proliferating lung epithelial cells. For example, both the dividing and non-dividing lung epithelial cell types can be targeted by pseudotyped retroviral vectors carrying a wild type CFTR cDNA.

CF patients have CFTR mutations that leads to basic chloride flux defect in the respiratory ciliated epithelial cells. This CFTR dysfunction causes chronic infection and inflammation of the respiratory tract and leads to high morbidity and mortality in CF patients. The CFTR cDNA gene transfer by adenoviral vectors or liposomes has demonstrated partial correction of the defective CFTR channel activity in the nasal epithelium of CF patients. Recent studies suggest that gene therapy may offer great benefits to CF patients even if only partial correction of CFTR gene function is achieved.

In some embodiments, a neurogenetic or neurodegenerative (i.e., a degenerative or inherited disorder of the nervous system) disorder can be treated by contacting a cell or administering to a subject (e.g., a mammal) a transgene. The transgene can be contained within a virion (e.g., a pseudotyped retrovirus virion containing a LCMV strain WE-54 envelope glycoprotein and the transgene), or a vector (e.g., a vector containing (a) a nucleic acid that encodes an envelope glycoprotein from Lymphocytic Choriomeningitis Virus strain WE-54, and (b) the transgene). Any suitable method can be used to contact a cell (e.g., a neural cell from an area of the central nervous system such as the ependyma, choroids plexus, subventricular zone (SVZ), rostral migratory stream (RMS), or olfactory bulb (OB)). The cell can be contacted in vitro, ex vivo, or in vivo, such as when a subject is directed treated with a virion or a vector as described herein. Further, any suitable method can be used to administer a virion or a vector to a subject diagnosed with a neurogenetic disorder. Neurogenetic disorders that can be treated using such methods include, without limitation, lysosomal storage diseases (e.g., leukodystrophies, mucopolysaccharidoses, and ceroid lipofuscinoses), Huntington's disease, Parkinson's disease, amyotrophic lateral sclerosis, ataxias, dentatorubral-pallidoluysian atrophy, prion disease, and Alzheimer's disease.

cancer: cancers may be treated with vectors carrying genes that express cancer antigens, or immunomodulatory proteins, and thereby stimulate an immune response against the cancer cells, or express a normal tumor suppressor gene to replace the function of a mutated, tumor-prone gene, such as a p53 mutant.

In addition to replacement of defective genes, it has been proposed that viral vectors could be used to deliver genes designed to stimulate immunity against or to otherwise destroy tumor cells. Although the integration of therapeutic genes into tumor cells is not required for cancer gene therapy application in most cases, sustained expression of the therapeutic genes in tumor cells may be required, for example, to elicit a long lasting in vivo anti-tumor immunity.

Gene therapy, originally developed for treating inherited and acquired diseases by introducing therapeutic genes to somatic cells, has great potential for cancer treatment. There are three major components to be considered in the design and development of a gene therapy regimen: the therapeutic genes, the mode of gene delivery (ex vivo or in vivo), and an appropriate preclinical study model for the assessment of the therapeutic efficacy. Various therapeutic genes have been utilized in cancer treatments. The common examples include: (1) genes that are capable of changing the cellular sensitivity to chemo- or radiation therapy in cancer patients either to sensitize tumor cells, or to minimize the damage of chemotherapy to normal cells such as the hematopoietic stem cells, (2) genes that interfere with proliferating tumor cell cycle by either replacing the mutated genes (i.e., tumor suppresser genes and apoptotic genes), or inactivating the oncogenes to prevent further tumor development, and (3) genes that can augment a systemic anti-tumor immunity in cancer patients; this can be accomplished by the injection of modified tumor infiltrating lymphocytes (TIL) or immunomodulatory gene-modified tumor cells, or by the modification of antigen presenting cells (APC). Retroviral vectors containing genes encoding tumor necrosis factor (TNF) or interleukin-2 (IL-2) have been transferred into tumor-infiltrating lymphocytes in patients [Kasid et al., *Proc. Natl. Acad. Sci. USA.* 87:473-477 (1990); and Rosenberg, *Human Gene Therapy* 5:140 (1994)]. It is postulated that the secretion of TNF or IL-2 stimulates a tumor-specific immune response resulting in the destruction of the tumor or the recruitment of effective tumor infiltrating lymphocytes from nearby lymph nodes. Other proposed anti-tumor gene therapy strategies include the delivery of toxin genes to the tumor cell.

Applications of antisense genes or oligonucleotides in inhibition of oncogenes and modulation of growth factors have the potential to reduce the mortality of cancer, in particular, human leukemia [For review see, Gewirtz, *Stem Cells* 3:96 (1993); and Neckers and Whitesell, *Amer. J. Physiol.,* 265:L1 (1993)].

HIV: vectors may be used to deliver transgenes that protect susceptible cells against HIV by synthesizing proteins, antisense RNAs, or ribozymes that block HIV binding and entry, reverse transcription, integration, or replication. Of course, the transgenes must be regulated so they do not interfere with the packaging of the transgene vector.

Selectable and Screenable Markers

A vector may contain one or more selectable or screenable markers. Such markers are typically used to determine whether the vector has been successfully introduced into a host or target cell. A selectable marker is a gene whose expression substantially affects whether a cell will survive under particular controllable conditions. A selectable marker may provide for positive selection (cells with the marker are more likely to survive), negative selection (cells with the marker are less likely to survive), or both (the choice of environmental condition dictating whether positive or negative selection occurs).

Selectable markers include those that confer antibiotic resistance (or sensitivity), the ability to utilize a particular nutrient, and resistance (or sensitivity) to high (or low) temperature. Suitable selectable markers include the bacterial neomycin and hygromycin phosphotransferase resistance genes, which confers resistance to G418 and hygromycin, respectively, the bacterial gpt gene, which allows cells to grow in a medium containing mycophenolic acid, xanthine and aminopterin; the bacterial hisD gene that allows cells to grow in a medium lacking histidine but containing histidinol; the multidrug resistance gene mdr; the hprt and HSV thymidine kinase genes, which allow otherwise hprt- or tk-cells to grow in a medium containing hypoxanthine, amethopterin and thymidine, and the bacterial genes conferring resistance to puromycin or phleomycin. Positive or negative selection may require the use of a particular strain of host cell for the selection to be effective.

Screenable markers are genes that encode a product whose presence is readily detectable, directly or indirectly, but do not necessarily affect cell survival. The green fluorescent protein (GFP) is an example. Any cell surface protein not native to the host cell can be used as an immunoscreenable marker. Transformed cells may be segregated out by using a fluorescent antibody to the protein and a cell sorter. Many enzyme-encoding genes are useful as screenable markers, especially those encoding enzymes that can act upon a substrate to provide a colored or luminescent product. The luciferase and beta-galactosidase genes have been especially popular.

A dominant marker encodes an activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant activity. Examples of non-dominant selectable markers include the thymidine kinase (tk) gene that is used in conjunction with tk cell lines, the CAD gene that is used in conjunction with CAD-deficient cells and the mammalian hypoxanthine-guanine phosphoribosyl transferase (hprt) gene that is used in conjunction with hprt-cell lines.

A review of the use of markers in mammalian cell lines is provided in Sambrook, et al., *Molecular Cloning: A Laboratory Manual* ($2^{nd}$ ed.), Cold Spring Harbor Laboratory Press, New York (1989) pp. 16.9-16.15.

Regulation of Gene Expression

The transgene(s) of the transgene vector, and the marker(s) and viral genes (or replacements) of the packaging and transgene vectors, and the glycoprotein genes of the envelope vector are expressed under the control of regulatory elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. A constitutive promoter is one that is always active at essentially a constant level.

Transcriptional control signals in eukaryotes comprise "promoter" and "enhancer" elements. Promoters and enhancers consist of short arrays of DNA sequences that interact specifically with cellular proteins involved in transcription [Maniatis et al., *Science* 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review, see, Voss et al., *Trends Biochem. Sci.*, 11:287 (1986); and Maniatis et al., supra (1987)). For example, the SV40 early gene enhancer is very active in a wide variety of cell types from many mammalian species and has been widely used for the expression of proteins in mammalian cells [Dijkema et al., *EMBO J.* 4:761 (1985)]. Two other examples of promoter/enhancer elements active in a broad range of mammalian cell types are those from the human elongation factor 1α gene [Uetsuki et al., *J. Biol. Chem.*, 264:5791 (1989); Kim et al., *Gene,* 91:217-223 (1990); and Mizushima and Nagata, *Nuc. Acids. Res.*, 18:5322 (1990)] and the long terminal repeats of the Rous sarcoma virus [Gorman et al., *Proc. Natl. Acad. Sci. USA,* 79:6777 (1982)] and the human cytomegalovirus [Boshart et al., *Cell* 41:521-530 (1985)].

As used herein, the term "promoter/enhancer" denotes a segment of DNA that contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of that gene is directed by the linked enhancer/promoter.

A regulatable promoter is one whose level of activity is subject to regulation by a regulatory molecule. An inducible promoter is one that is normally substantially inactive, but that is activated by the binding of an inducer to an operator site of the promoter. A repressible promoter is one that is normally active, but that is substantially inactivated by the binding of a repressor to an operator site of the promoter. Similar terminology applies to enhancers.

The inducer or repressor molecules are typically expressed only in particular tissues, at a particular developmental stage, or under particular environmental conditions (e.g., damage to the cell, infection, overproduction of a metabolite, absence of a nutrient). In the absence of an inducer an inducible promoter may be inactive or may produce a low level of activity. The level of activity in the presence of the inducer will be higher than the basal rate. A tightly inducible promoter is one whose basal level of activity is very low, e.g., less than 10% of its maximum inducible activity.

Different promoters may have different levels of basal activity in the same or different cell types. When two different promoters are compared in a given cell type in the absence of any inducing factors, if one promoter expresses at a higher level than the other it is said to have a higher basal activity.

The activity of a promoter and/or enhancer is measured by detecting directly or indirectly the level of transcription from the element(s). Direct detection involves quantitating the level of the RNA transcripts produced from that promoter and/or enhancer. Indirect detection involves quantitation of the level of a protein, often an enzyme, produced from RNA transcribed from the promoter and/or enhancer. A commonly employed assay for promoter or enhancer activity utilizes the chloramphenicol acetyltransferase (CAT) gene. A promoter and/or enhancer is inserted upstream from the coding region for the CAT gene on a plasmid; the plasmid is introduced into a cell line. The levels of CAT enzyme are measured. The level of enzymatic activity is proportional to the amount of CAT RNA transcribed by the cell line. This CAT assay therefore allows a comparison to be made of the relative strength of different promoters or enhancers in a given cell line. When a promoter is said to express at "high" or "low" levels in a cell line this refers to the level of activity relative to another promoter that is used as a reference or standard of promoter activity.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is one that is isolated from one gene and placed 3' of another gene. A commonly used heterologous poly A signal is the SV40 poly A signal. The SV40 poly A signal is contained on a 237 bp Bam HI/Bcl I restriction fragment and directs both termination and polyadenylation [Sambrook et al., supra].

The cytomegalovirus immediate early promoter-enhancer (CMV-IE) is a strong enhancer/promoter. [See, Boshart et al., supra.] Another strong promoter-enhancer for eukaryotic gene expression is the elongation factor 1α promoter enhancer. [See, Kim et al., supra; and Mizushima and Nagata, supra.]

The internal promoter for a transgene may be the promoter native to that transgene, or a promoter native to the target cell (or viruses infecting the target cell), or another promoter functional in the target cell.

The promoters and enhancers may be those exhibiting tissue or cell type specificity that can direct the transgene expression in the target cells at the right time(s). For example, a promoter to control human preproinsulin must be operable under control of carbohydrate in the liver. An example of such a promoter is the rat S-14 liver-specific promoter.

Promoters (and enhancers) may be naturally occurring sequences, or functional mutants thereof, including chimeras of natural sequences and mutants thereof. For example, a tissue-specific, development-specific, or otherwise regulatable element of one promoter may be introduced into another promoter.

Chen et al, *Proc. Nat. Acad Sci USA,* 93:10057-10062 (1996) placed a VSV-G gene under the control of a tetracycline-inducible promoter and also expressed a fusion of the ligand binding domain of the estrogen receptor to a chimeric transcription factor, tTA, obtained by fusing the tet repressor (tetR) and the activation domain of HSV virion protein 16.

For the ability to replace the endogenous 5' LTR promoters and enhancers with heterologous ones, such as CMV immediate-early enhancer-promoter [see, Chang, et al., *J. Virol.,* 67: 743-52 (1993)].

Vector; Transfection of Vectors

As used herein, the term "vector" is used in reference to nucleic acid molecules that can be used to transfer nucleic acid (e.g., DNA) segment(s) from one cell to another. The term "vehicle" is sometimes used interchangeably with "vector." It is intended that any form of vehicle or vector be encompassed within this definition. For example, vectors include, but are not limited to viral particles, plasmids, and transposons.

The term "transfection" as used herein refers to the introduction of foreign DNA into eukaryotic cells. Transfection may be accomplished by a variety of means known to the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Vectors may contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high copy number (up to $10^4$ copies/cell) in cells that express the appropriate viral T antigen. Vectors containing the replicons from bovine papillomavirus or Epstein-Barr virus replicate extrachromosomally at low copy number (about 100 copies/cell).

Expression Vector

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In some embodiments, "expression vectors" are used in order to permit pseudotyping of the viral envelope proteins.

Host Cells

The host cell is a cell into which a vector of interest may be introduced and wherein it may be replicated, and, in the case of an expression vector, in which one or more vector-based genes may be expressed.

It is not necessary that the host cell be injectable by the transgene vector virions of the present invention. Indeed, in some examples they not be so injectable, so the host cells do not bind the virions and thereby reduce the vector production titer. This can be achieved by choosing (or engineering) cells that do not functionally express the receptor to the vector particle envelope protein.

Target Cells and Organisms

The transgene vector may be administered to a target organism by any route that will permit it to reach the target cells. Such route may be, e.g., intravenous, intratracheal, intracerebral, intramuscular, subcutaneous, or, with an enteric coating, oral. Alternatively, target cells may be removed from the organism, infected, and they (or their progeny) returned to the organism. Or the transgene vector may simply be administered to target cells in culture.

The target cells into which the transgene is transferred may be any cell that the transgene vector, after packaging into a virion, is capable of infecting, and in which the control sequences governing expression of the transgene are functional. Generally speaking, it will be a eukaryotic cell, such as a vertebrate cell (e.g., a cell of a mammal or bird). If a mammal, the mammal may belong to one of the orders Artiodactyla (e.g., cows, pigs, goats, sheep), Perissodactyla (e.g., horses), Rodenta (e.g., rats, mice), Lagomorpha (e.g., rabbits), Carnivora (e.g., dogs, cats) or Primata (e.g., humans, apes, monkeys, lemurs). If a bird, it may be of the orders Anseriformes (e.g., ducks, geese, swans) or Galliformes (e.g., quails, grouse, pheasants, turkeys, chickens). In one embodiment, it will be a human cell. The cells in question may be dividing or non-dividing cells. Non-dividing cells of particular interest include airway epithelial cells, nervous system (e.g., central nervous system) cells, or hepatocyte cells. Examples of nervous system cells include, without limitation, neurons, glia (e.g., astrocytes), and progenitor cells.

Dividing cells of particular interest include hematopoietic stem cells, muscle cells, white blood cells, spleen cells, liver cells, epithelial cells, and eye cells.

TE671, HepG2, HeLa, 293T, and MT4 are of particular interest for experimental studies. TE671 rhabdomyosarcoma cells can be induced to differentiate into muscle cells by HIV-1 Vpr. HepG2 hepatoma, HeLa cervical carcinoma, 293T human kidney carcinoma and MT4 lymphoma cells are all transformed by HTLV-I human T cell leukemia virus type I. MT4 cells are very susceptible to wild-type HIV-1 NL4-3 and hence have been used as indicator cell for RCV.

Miscellaneous Definitions

As used herein, the term "endogenous virus" is used in reference to an inactive virus that is integrated into the chromosome of its host cell (often in multiple copies), and can thereby exhibit vertical transmission. Endogenous viruses can spontaneously express themselves and may result in malignancies.

The term "gene" refers to a DNA sequence of a vector or genome that comprises a coding sequence and is operably linked to one or more control sequences such that, in a suitable host cell, under suitable conditions, a biologically active gene product, or a gene product that is a precursor of a biologically active molecule, is produced that is encoded by the coding sequence. This gene product may be a transcriptional product, i.e., a messenger RNA, as in the case of an antisense RNA or a ribozyme. Or it may be a translational product, i.e., a polypeptide (the term "polypeptide" as used herein includes oligopeptides), which is either biologically active in its own right, or further processed by the cell to generate one or more biologically active polypeptide products. In the case of retroviruses, where the genome is RNA, the term "gene" also refers to the RNA sequence of the retroviral genome that a suitable host cell reverse transcribes into a DNA sequence that acts as a gene in the classic sense.

Depending on context, the term "gene" may refer to the DNA sequence encoding a single mRNA transcript, or only to that portion of the DNA sequence that is ultimately expressed as a single polypeptide chain.

In the vectors of the present invention, each gene may be constructed from genomic DNA, complementary DNA (DNA reverse transcribed from mRNA), synthetic DNA, or a combination thereof. The gene may duplicate a gene that exists in nature, or differ from it through the omission of introns (noncoding intervening sequences), a so-called minigene, silent mutations (i.e., mutations that do not alter the amino acid sequence of the encoded polypeptide), or translated mutations (i.e., mutations that do alter that sequence). In the latter case, the mutations may be functional mutations (ones that preserve at least a substantial portion of at least one of the biological activities or functions of the encoded polypeptide) or nonfunctional (inactivating) mutations.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

Assays

From time to time, one may wish to ascertain various information concerning the envelope, packaging and transgene vectors of the present invention.

One might like to know whether the vectors have become established in the cell; whether particular vector genes have integrated into the genome; whether the packaging cell line is producing viral proteins; whether those viral proteins are being assembled into viral particles; whether, in the absence of the transgene vector, those viral particles are essentially free of RNA, such as packaging vector RNA; whether recombination occurs between the packaging vector and the transgene vector, or between these two vectors and defective retroviruses endogenous to the host (or target) cell; whether such recombination, if any, produces replication-competent virus; whether recombinant virus is packaged by the packaging cell line; the efficiency with which the packaging cell line packages the transgene vector into the viral particles; whether the transgene vector-containing viral particles are infectious vis-a-vis the target cells; whether the latter particles are cytotoxic to the target cells; whether the latter particles are immunogenic to the target organism; whether infected target cells themselves produce viral RNA-containing particles, infectious or otherwise; and the level and duration of expression of the transgene in the target cells.

The successful establishment of the envelope, packaging or transgene vector in the host (or target) cell may be verified by selecting for the presence of a selectable marker, or screening for the presence of a screenable marker, carried by the vector. The integration of the relevant envelope, packaging or transgene vector genes may be determined by collecting genomic DNA, amplifying the gene of interest by PCR, and detecting the amplified sequence with a suitable hybridization probe. The production of viral proteins may be detected by an immunoassay; the sample may be a cell lysate or a cell supernatant. An immunoassay by itself cannot determine whether the viral proteins are produced in functional form, although there is greater assurance of this if the antibody used is directed to a conformational epitope, or is an activity-neutralizing antibody. One may alternatively detect the appropriate messenger RNA by means of a hybridization probe.

The functionality of the produced Gag and Env protein may be determined by examining the cell lysate or supernatant for the presence of viral particles; these may further be examined for proper morphology by means of an electron microscope. It is also possible that antibodies could be used that bind to the formed viral particles, but not to gp120 or gp41 by itself. The functionality of the Pol reverse transcriptase may be determined by assaying the viral particles for RT activity. The functionality of the Pol integrase is apparent only in assays that examine whether RNA from viral particles is integrated into the target cell.

Viral particles produced by the packaging cell line may be collected and assayed for total RNA content. If more specific information is desired as to the nature of any packaged RNA, a suitable hybridization probe may be employed.

In an infectivity assay, the vector is introduced into a first culture of susceptible cells. Then, either a second culture is layered onto the first, so that infectious particles may travel by cell-to-cell contact, or the second culture is exposed to the supernatant of the first culture. The cells of the first and second culture are examined for a least one of the following indicia: RT activity, p24 Gag antigen expression, production of viral particles, and cytotoxic effects. The stringency of the assay is dependent on the susceptible of the cells to infection and to cytotoxicity, and the time allowed for the recombination and spread of the virus in the first and second cultures. Typically, the infectivity of the vector or vector system will be compared with that of a wild-type, unattenuated, replication-competent retrovirus.

Animal studies may be used to ascertain the immunogenicity and pathogenicity of the vector system.

Measurement of Infectivity of Packaging Vector Per Se

The ability of a packaging vector to generate transmissible virus, as opposed to defective virus, may be measured. One method is described by Mann et al., *Cell*, 33:153-159 (1983). The packaging vector and its wild-type counterpart are independently transfected into suitable host cells, and reverse transcriptase activity in the culture supernatants is assayed over a period of days or weeks. A rapid increase in RT activity over 24-48 hrs is indicate of gene expression after transient transfection. A continued increase is indicative of the efficient spread of virus from the initially transfected cells to the remaining cells on the plate.

A slow or delayed increase could be indicative of either a steady but attenuated spread of virus, or to generation of competent virus by mutation, or by recombination with a cellular sequence capable of providing the missing function. To differentiate these possibilities, one may use various dilutions of culture supernatants from cells previously transfected (days or weeks before) with the vector (or with the control virus), use them to infect fresh cells, and monitor RT activity in the latter. If the latter cells develop high levels of RT activity, it suggests that non-defective virus was present in the transferred culture supernatant.

Measurement of Packaging Efficiency

The packaging efficiency of a packaging cell line in the presence or absence of the packageable transducing transgene vector may be measured in a variety of ways (see, e.g., Mann et al., supra). In essence, total cellular RNA is purified from the culture supernatant of the test and control cell lines, and viral RNA is extracted from purified viral particles released from the test and control cell lines. The two virion preparations are normalized by reference to their reverse transcriptase activity just prior to RNA extraction. The purified RNAs are probed with a virus-specific hybridization probe (e.g., a plasmid containing the entire viral genome) in a slot-blot assay, and the amount of viral RNA in the particles and in the cells is thereby quantified.

It is not unusual for the packaging efficiency of a packaging cell line to be less than 1% that of a host cell infected by wild-type virus.

Measurement of Packaging Specificity

It is also desirable that the packaging cell line be able to efficiently package the highly defective transgene vector into viral particles, and bud the particles into the culture supernatant (in vitro) or extracellular environment (in vivo) without also budding helper virus (the packaging vectors).

One method of measuring this packaging specificity is described by Mann et al. (supra). In essence, the transgene vector is transfected into the packaging (helper) cell line. After 24 hours, the culture supernatants are used to infect fresh potential host cells (reporter cells). Two days later, selection pressure for the transferred gene is applied, and 8-10 days later, the transferred gene-positive colonies or cells are counted. In addition, one determines the reverse transcriptase activity of the supernatant collected from the packaging cell lines, and the reverse transcriptase activity of the fresh cells. A transgene vector-specific packaging cell line will produce a high transfer gene activity and a low reverse transcriptase activity in the reporter cells. In addition, the reporter cells will not produce reporter gene-positive colony-forming units (cfus).

Measurement of Helper Activity

The ability of a packaging vector to provide all viral functions required in trans may be assayed by co-transfecting host cells with the packaging vector (or control virus) and with a reporter vector carrying a selectable reporter gene. After 24 hours, culture supernatants of the transfected cells are used to infect a second plate of host cells. Selection pressure for the reporter gene is applied, and reporter-positive colonies are counted. If the helper activity is of wild-type magnitude, the count for the packaging vector should be of the same order of magnitude as that for the control virus, and no reporter activity should be detectable in the second plate when the reporter vector or the control wild-type virus expressing all viral functions is transfected into the host cells of the first plate by itself.

Measurement of Generation of Replication-Competent Virus (RCV)

Several sensitive assays are available for the detection of RCV in the present retroviral vector systems. These include: (1) co-cultivation with a sensitive cell line such as MT4, AA2 or PBLs; (2) the CD4 HeLa MAGI cell assay that relies on Tat transactivation of an integrated LTR-lacZ gene; and (3) a sensitive immunohistochemical staining method for the detection of HIV antigen expression at the individual cell level.

RC-HIV can also be studied in an in vivo model by transduction of humanized SCID/beige mice. In the latter model, a long in vivo incubation time can be performed, mimicking the situation that exists in a human clinical trial. In addition, the possibility of generating HIV/HERV recombinants may be carefully tested using an artificially constructed HIV/HERV-env recombinant.

Virion Stability

Since one class of the therapeutic agents of the present invention would be the packaged transgene vectors, the stability of the packaged transgene vectors under adverse conditions, especially those that might be encountered during storage, is of interest. Thermostability may be ascertained by subjected them to elevated (e.g., 37° C.) or depressed (e.g., 4° C.) temperatures for various periods of time (e.g., 2, 4, 6 or 8 hrs., or overnight), or to a number (e.g., 1-6) freeze-thaw cycles, and determining the number of infectious particles remaining as a percentage of the number of such particles prior to treatment.

Assays for Immunogenicity

A method for determining whether the contemplated vectors, or their gene products, could elicit an immune response in a subject involves evaluating cell-mediated immunity (CMI) using either an immunocompetent mouse model or a humanized SCID/beige mouse model.

Using a modified hu-PBL-SCID mouse reconstitution protocol, an in vivo model for evaluating CMI against HIV-1 in humans has been developed. SCID/beige mice lacking T, B and natural killer (NK) cell functions are severely immunodeficient. This strain of mice can be successfully reconstituted with fresh human peripheral blood lymphocytes (PBLs), and exhibits functional human naive, memory and activated T cell markers for more than 2-3 months. In these experiments, spleen and peripheral blood lymphocytes were harvested 38 days after reconstitution from reconstituted SCID/beige mice, and red blood cells were lysed prior to incubation with anti-mouse 2Kd, anti-human CD45, anti-human CD3, anti-human CD4 and anti-human CD8 labeled antibodies. Reconstituted human lymphoid cell populations in the spleen and in the peripheral blood of the SCID/beige mice can reach up to 50-80% and 5-12%, respectively.

For the immune response study, mice repetitively injected with the viral vectors will be analyzed. Their sera will be assayed for Ab response to viral antigens, such as p24 Gag or the pseudotype env. For cell-mediated immune response study, the mouse splenocytes will be isolated and an in vitro assay for cellular immunity will be performed as described below. T cell response to recall antigen is normally characterized by the production of interferon gamma (IFN$\gamma$). This assay requires activation of lymphocytes with the test Ags, such as Gag p24 or Gag-Pol or env proteins of the vector.

Upon activation, the Th1 lineage of T cells produce interferon gamma (IFN-$\gamma$) and the measurement of IFN-$\gamma$ production has been shown to be a reliable assay for CMI. Thus, for example, to determine CMI against HIV-1 using the in vivo humanized SCID/beige mouse model, a sensitive ELISPOT assay for the detection of IFN-$\gamma$ producing cells was developed. With the computer assisted imaging system integrated into this protocol, the ELISPOT method was shown to be very convenient and more sensitive than the conventional limiting dilution assay for the determination of the effector T cell precursor frequency. This in vivo model and the ELISPOT assay system were developed for the evaluation of in vivo CMI after lentiviral gene transfer. See, e.g., PCT/US98/06944.

Pseudotyping Retroviral Vectors with Novel Envelope Glycoproteins to Enhance Target Cell Transduction.

Retroviral vector-mediated gene transfer begins with the attachment of the virion to a specific cell surface receptor

[Goff, *J Gene Med.* 3:517-528 (2001)]. This attachment is the first step in the entire gene transfer process and a crucial factor in determining vector tropism and the range of target tissues/cell types. Vector binding is mediated by specific interactions between the envelope glycoproteins on the virion and one or more surface receptor molecules on the target cell. If this receptor molecule is absent (as when its expression is specific for certain cell types) or is variant in the binding region (such as in species other than the natural host), gene transfer cannot occur [Coffin et al. *Retroviruses*. Plainview: Cold Spring Harbor Press, 2000]. By replacing the native envelope protein with other retroviral or non-retroviral glycoproteins, a process termed "pseudotyping", one can alter the host range of the vectors, which can result in increased transduction efficiency of desirable target cells [Miller, *Proc. Natl. Acad. Sci. USA,* 93:11407-11413 (1996)].

The vesicular stomatitis virus (VSV-G) and the amphotropic envelope proteins are the two most commonly used glycoproteins for retroviral/lentiviral-based gene transfer. However, for many cell types the transduction efficiency using both envelope glycoproteins is low. Moreover, both envelopes have limitations for potential clinical applications. For example, VSV-G is cytotoxic [Park et al., *Blood* 96:1173-1176 (2000); Stewart et al., *Proc. Natl. Acad. Sci. USA* 96:12039-12043 (1999)] and may be inactivated by human serum [DePolo et al., *Mol. Ther.,* 2:218-222 (2000)] and the amphotropic glycoprotein is fragile and does not tolerate centrifugation concentration as well as VSV-G [Burns et al, *Proc. Natl. Acad. Sci. USA,* 90:8033-8037 (1993)]. In an effort to increase the in vivo gene transfer efficiency of lentiviral vectors to cells and tissues for therapeutic gene delivery, the FIV vector was pseudotyped with viral envelope glycoproteins from non-retroviral enveloped viruses. The gene transfer efficiency of these pseudotyped vectors were evaluated in several cells and tissues including airway epithelia, lung, brain, and liver.

Pseudotyping Retroviral Vectors with LCMV Envelope Glycoproteins.

The present invention provides a method to pseudotype retroviruses to attain high titers suitable for ex vivo and in vivo gene transfer using envelope glycoproteins from lymphocytic choriomeningitis virus (LCMV) strain WE54. This invention is useful for gene therapy applications using retroviral vectors. The methods described in this disclosure provide a novel way to increase the transduction efficiency and target specific cell types that were previously poorly accessible with existing vector envelopes. In particular these methods have applications for targeting tissues such as airway epithelia, neural progenitors in the CNS, hepatocytes and others.

Further methods described herein allow for modification of specific amino acid residues of the glycoproteins to further enhance transduction efficiency. The methods facilitates the production of stable packaging cell lines for vector production.

The invention disclosed has applications to the field of gene therapy. The approaches described overcome previous limitations efficiently transducing cells with retroviral vectors using glycoproteins from enveloped viruses. The LCMV-WE54 pseudotyped vector has applications for diseases affecting airway epithelia (i.e., cystic fibrosis), the CNS (i.e., neurodegenerative or neurogenetic disorders), and hepatocytes (i.e., hemophilia).

The inventors initially documented that the LCMV envelope from WE54 strain (also called WE-HPI) was compatible with production of the non-primate lentiviral vector feline immunodeficiency virus based vector (FIV). Titers were sufficiently high to permit in vitro and in vivo studies. The inventors documented that the LCMV-WE54 pseudotyped vector transduced human airway epithelia much more efficiently from the apical rather than the basolateral surface in vitro. Subsequently, a single point mutation (L260F) was made in the glycoprotein. Vector preparations with this modified LCMV-WE54 envelope transduced airway epithelia with ~10-fold greater efficiency than the wild type envelope. The efficiency of gene transfer with the L260F LCMV-WE54 envelope is greater than that obtained with several other conventional envelopes.

Additional mutants including S153F and the double mutant L260F/S153F are made. These changes are made to reduce the affinity of the vector to one identified receptor called alpha-dystroglycan.

As described in the Examples below, experiments in cultured human airway epithelia, mouse liver, and mouse brain document that the vector is functional for in vivo gene transfer. Additional experiments showed transduction of cells in olfactory bulb (OB) brain cells following intrastriatal injection in mice, and indicated that the vector transduced neural progenitor cells that migrated from the striatum to the OB. Intravenous injection of the vector in the mouse resulted in significant transduction of the liver, including hepatocytes.

Methods of Preparing Retroviral Vectors

Recombinant retroviruses can be produced by a number of methods. One method is the use of packaging cell lines. The packaging cells are provided with viral protein-coding sequences, such as encoded on two three plasmids [Johnston et al., *J. Virol.,* 73:4991-5000 (1999)]. The plasmids encode all proteins necessary for the production of viable retroviral particles and encode a RNA viral construct that carries the desired gene (e.g., the gene encoding the mutant envelope protein or a mutant envelope fusion protein), along with a packaging signal (Ψ Psi) that directs packaging of the RNA into the retroviral particles.

Alternatively, the mutated retroviral genome can be transfected into cells using commonly known transfection methods such as calcium chloride, electroporation, or methods described in the examples. [See also, Sambrook et al. *Molecular Cloning: A Laboratory Manual* ($2^{nd}$ ed.), Cold Spring Harbor Laboratory Press (1989).]

The retroviral vector may also include an appropriate selectable marker. Examples of selectable markers that may be utilized in either eukaryotic or prokaryotic cells, include but are not limited to, the neomycin resistance marker (neo), the ampicillin resistance marker (amp), the hygromycin resistance marker (hygro), the multidrug resistance (mdr) gene, the dihydrofolate reductase (dhfr) gene, the beta-galactosidase gene (lacZ), and the chloramphenicol acetyl transferase (CAT) gene.

Cells transfected with cDNAs encoding a retrovirus genome or infected with retrovirus particles can be cultured to produce virions or virus particles. Virus particle-containing supernatant can be collected. The virus particles can be concentrated by centrifuging the supernatant, pelleting the virus and by size exclusion chromatography. Pharmaceutical compositions containing virus particles can also be resuspended in pharmaceutically acceptable liquids or carriers such as saline.

Retroviral Gene Transfer

The retrovirus particles described above can infect cells by the normal infection pathway as along as recognition of the target cell receptor, fusion and penetration into the cell all occur. All eukaryotic cells are contemplated for infection by the recombinant virions. For example, the cells used in the present invention can include cells from vertebrates (e.g., human cells).

The vectors of the present invention can be used in vivo with a number of different tissue types. Examples include airway epithelia, liver, and neural (e.g., central nervous system) cells. Methods for infecting cells with retrovirus particles are described generally in *Gene Therapy Protocols: Methods In Molecular Medicine*, Paul D. Robbins (ed.) (Humana Press, 1997). Other methods of preparing and administering retroviral particles in gene therapy commonly known to the skilled artisan may be used.

The types of genes that are to be transferred into the host cell by the retrovirus particles of this invention may encode therapeutic agents, enzymes, growth factors, cell receptors, suicide or lethal genes.

Such genes or nucleic acid molecules are under the control of a suitable promoter. Suitable promoters, which may be employed, include, but are not limited to adenoviral promoters, the cytomegalovirus promoter, the Rous sarcoma virus (RSV) promoter, the respiratory syncytial virus promoter, inducible promoters such as the metallothionein promoter, heat shock promoters, or the gene's own natural promoter. It is to be understood however, that the scope of the present invention is not to be limited to specific foreign genes or promoters.

Most gene therapy is administered to cells ex vivo. The cells receiving such gene therapy treatment may be exposed to the retrovirus particles in combination with a pharmaceutically acceptable carrier suitable for administration to a patient. The carrier may be a liquid carrier (for example, a saline solution), or a solid carrier such as an implant or microcarrier beads. In employing a liquid carrier, the cells may be introduced intravenously, subcutaneously, intramuscularly, intraperitoneally, intralesionally, etc. In yet another embodiment, the cells may be administered by transplanting or grafting the cells. Lipid destabilizers, such as thiocationic lipids, can be utilized in admixture with the viral vector or liposomal vector to increase infectivity (see examples of lipid destabilizers in U.S. Pat. Nos. 5,739,271 and 5,711,964).

Although most current gene therapy protocols involve ex vivo transfection of cells, the vectors disclosed would permit in vivo treatment of a subject, such as a human patient, as well as ex vivo utilization. For example, ex vivo therapy requires that cells such as hepatocytes be removed from the patient, transduced with the retroviral particle containing the desired nucleic acid molecule, and then transplanted back into the patient. In vivo therapy would allow direct infusion of the gene therapy vector, without the intervening steps and the complications that they raise. Moreover, this will allow access to tissues that may not have been good candidates for ex vivo gene therapy.

Virus Particles

Gene therapy vectors also include pseudotyped virus particles. Pseudotype viruses were originally created to overcome problems encountered by gene therapy vectors' natural host cell tropisms. In recent years, many gene therapy patents have issued wherein the vector contains a heterologous polypeptide used to target the vector to specific cells, such as vectors containing chimeric fusion glycoproteins (U.S. Pat. No. 5,643,756); vectors that contain an antibody to a virus coat protein (U.S. Pat. No. 5,693,509); viruses engineered to allow study of HIV-1 in monkeys, a species that normally cannot be infected by HIV-1, by creating hybrid viruses (U.S. Pat. No. 5,654,195); and pseudotype retrovirus vectors that contain the G protein of Vesicular Stomatitis Virus (VSV) (U.S. Pat. Nos. 5,512,421 and 5,670,354). In the current invention an exemplary envelope protein is baculovirus GP64, and related envelopes.

The invention will be further described in the following examples, which do not limit the scope of the invention described in the claims.

EXAMPLES

Example 1

LCMV Pseudotyped FIV Targets the Apical Surface of Airway Epithelia for Entry

The inventors evaluated the ability of LCMV glycoproteins (GPs) to pseudotype the FIV vector. LCMV-GP is initially expressed as a precursor polypeptide, GP-C, which is post-translationally processed by a cellular protease into GP1 and GP2. GP1 mediates binding to the cellular receptor for LCMV, and GP2 contains the fusion peptide and the transmembrane region [Buchmeier et al., supra]. Recently Beyer and colleagues reported successful pseudotyping of HIV-based lentivirus vectors with glycoproteins from the LCMV WE54 strain [Beyer et al., *J. Virol.* 76:1488-1495 (2002)]. In contrast to amphotropic-MLV vector particles, LCMV pseudotypes could be efficiently concentrated by ultracentrifugation without loss of vector titer. The inventors obtained the LCMV strain WE54 GP from Dr. Beyer and evaluated its efficiency in pseudotyping FIV. Titers for the FIV pseudotyped with LCMV WE54 were ~$5 \times 10^8$ TU/ml, very suitable for in vitro and in vivo studies.

Figure 1:
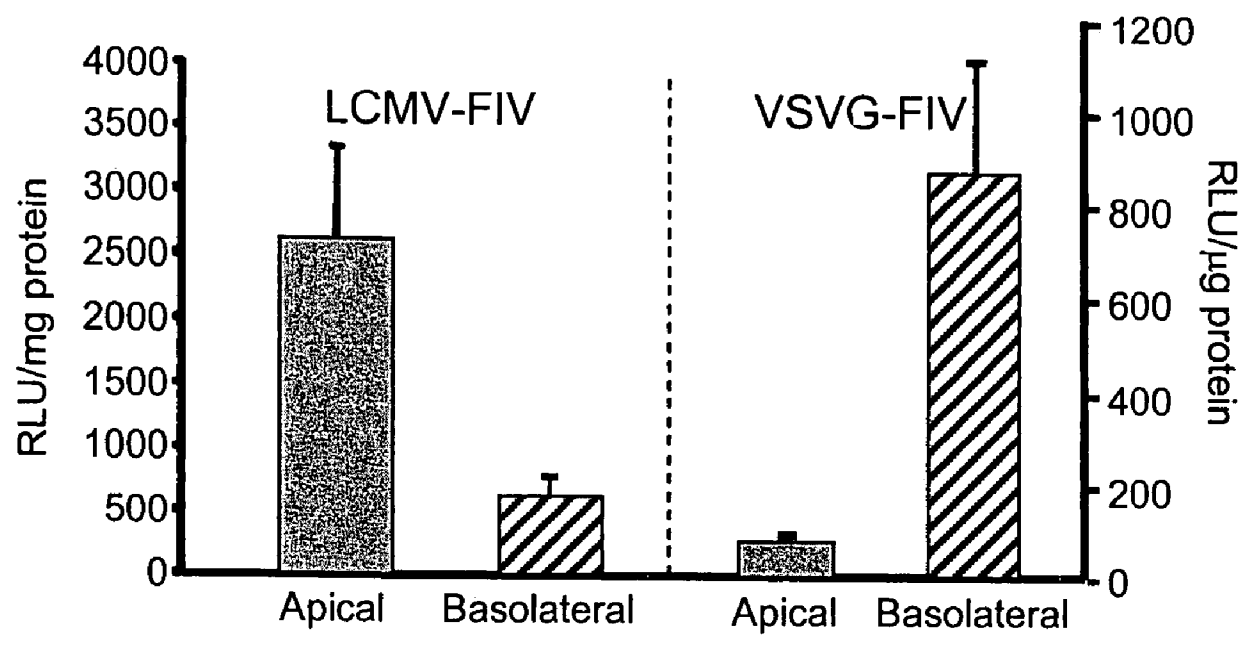

High titer FIV pseudotyped with the LCMV-WE54 GPs was evaluated for its ability to transduce primary cultures of well-differentiated human airway epithelia. The vector was applied to the apical or basolateral surface of the epithelial sheet at an MOI of ~5. For comparison, VSVG-FIV results from previous studies are shown [Sinn et al., *J. Virol.* 77:5902-5910 (2003)]. Four days later, gene transfer was quantified by measuring beta-galactosidase activity as described previously [Sinn et al., supra]. As shown in FIG. 1, while the LCMV pseudotyped vector transduced the cells from either surface, the apical efficiency was significantly greater than basolateral. This finding is the opposite of the inventors' findings with the VSV-G envelope, where entry is predominantly basolateral [Sinn et al., supra; Wang et al., *J. Clin. Invest.* 104:R49-R56 (1999)]. It is important to note that at the same MOIs, the beta-galactosidase enzyme activity levels for the LCMV vector were similar to those achieved with the VSV-G envelope, the most efficient pseudotype we have identified to date. Gene transfer was inhibited by the reverse transcriptase inhibitor AZT, indicating that these results do not represent protein transfer or pseudotransduction.

Figure 2:
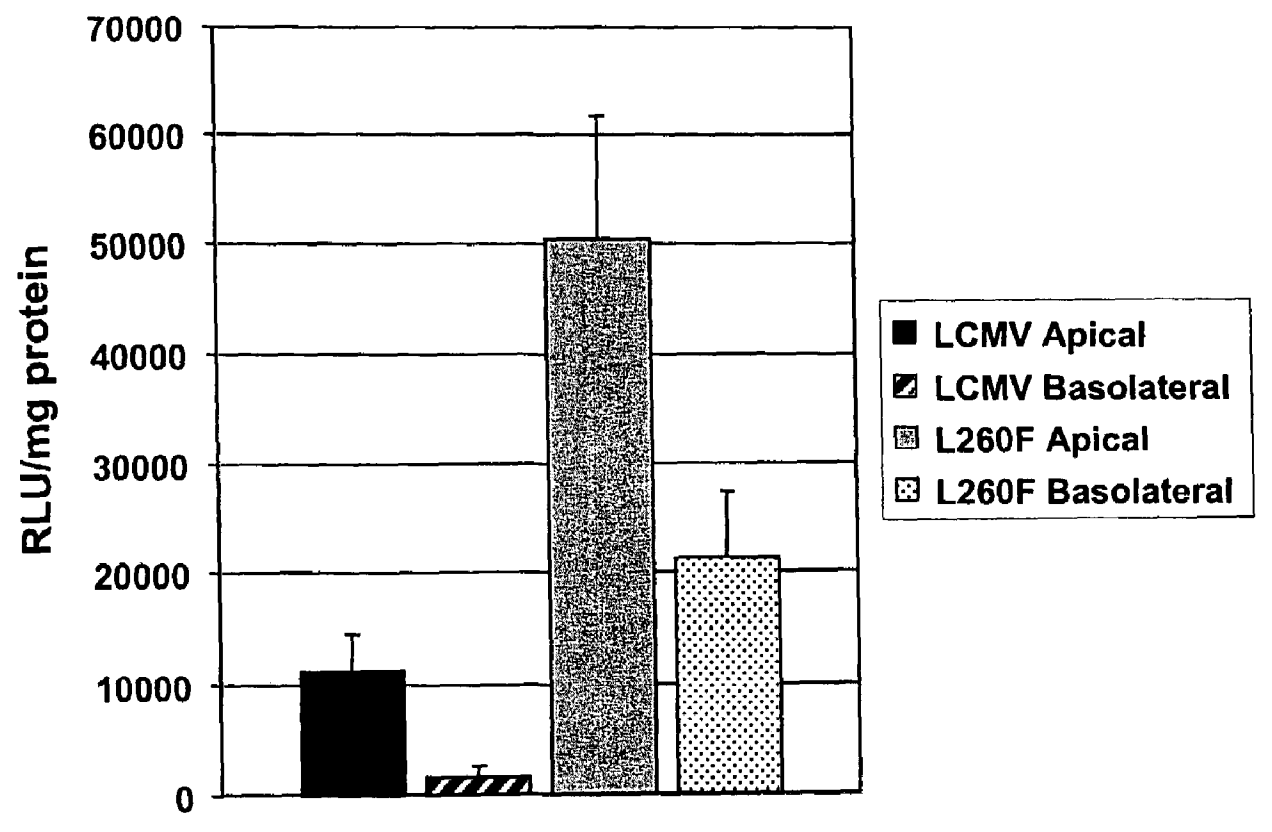

Arenaviruses using alpha-DG as their major receptor have the small aliphatic amino acids leucine or isoleucine at position 260 in GP1 and a bulky aromatic amino acid, phenylalanine or tyrosine, at position 259 of GP1 [Spiropoulou et al., *J. Virol,.* 76:5140-5146 (2002)]. While the receptor for the LCMV-WE54 strain the inventors used to pseudotype FIV has not been identified in airway epithelia, the LCMV-WE54 strain has an F at position 259 and an L at position 260, and is predicted to bind alpha-DG with high affinity. The inventors hypothesized that FIV pseudotyped with wild type LCMV-WE54 GPs uses alpha-DG as a high affinity receptor for initial binding steps in polarized human airway epithelia. The inventors mutated the L at position 260 in the LCMV-WE54 envelope to an F (L260F) [Spiropoulou et al., supra] to test its importance in directing LCMV WE54 transduction of differentiated human airway epithelia. Both WE54 and the L260F mutants pseudotype FIV with comparable high titers. FIG. 2 shows the gene transfer efficiency of FIV pseudotyped with these two envelopes following apical or basolateral application to well-differentiated primary cultures of human airway epithelia. The L260F variant transduces the cells much more efficiently than WE54 and maintains an apical preference for entry.

Example 2

Receptors for LCMV

Alpha-dystroglycan (alpha-DG) was identified as a high affinity receptor for several arenaviruses including some strains of LCMV, Lassa virus, Oliveros virus, and Latino virus [Cao et al., *Science,* 282:2079-2081 (1998)]. Dystroglycan is a dystrophin-associated glycoprotein that connects the cytoskeleton with the extracellular matrix and is widely expressed in most tissues, including the lung [Henry and Campbell, *Cell,* 95:859-870 (1998); White et al., *Am. J. Respir. Cell. Mol. Biol.* 24:179-86 (2001)]. Dystroglycan is post-translationally cleaved into a highly glycosylated peripheral membrane protein alpha-DG, which is noncovalently associated with the membrane-spanning protein beta-dystroglycan [Henry and Campbell, *Curr. Opin. Cell Biol.,* 11:602-607 (1999)]. Beta-dystroglycan is linked to the cytoskeleton. It is important to note that studies with wild type LCMV WE54 strain demonstrate high affinity binding to alpha-DG (Spiropoulou et al., supra). However, some LCMV variants (e.g., Armstrong strain) inefficiently interact with alpha-dystroglycan and also infect dystroglycan-negative cells. Therefore, there appears to be at least one additional, currently unknown receptor or co-receptor for LCMV [Spiropoulou et al., supra].

To investigate the potential role for alpha-dystroglycan as a receptor for LCMV pseudotyped FIV, the inventors evaluated the ability of laminin, IIH6 antibody, or cell culture media containing shed alpha dystroglycan to inhibit gene transfer to airway epithelia with the WE54 or L260F pseudotypes. Work of others indicated that the WE54 GP1 binds alpha DG with high affinity. Cells were treated with the respective reagents for one hour prior to application of vector (MOI=1) and throughout the four hour application period. As shown in FIG. 3, each of these reagents had a small inhibitory effect on WE54, with the greatest blocking effect coming from the cell culture media. None of the agents affected gene transfer with the L260F pseudotype. The findings support the notion that wild type WE54 has affinity for alpha DG while the L260F pseudotype has little or no affinity for alpha DG. Thus, while the FIV-WE54 LCMV pseudotype may bind to alpha DG with some affinity, there is most likely another receptor or co-receptor involved in the transduction of airway epithelia. Furthermore, alpha DG does not appear to be an important receptor for the L260F variant.

Example 3

Gene Transfer to Mouse Liver Using FIV Pseudotyped with LCMV Envelope

Gene transfer to the liver has potential clinical applications for many diseases. The inventors evaluated the liver transduction properties of the FIV pseudotyped with LCMV-L260F. For systemic vector delivery to the liver, C57BL/6 mice received the LCMV pseudotyped FIV vector intravenously via the tail vein using methods as previously described [Stein et al., *Mol. Ther.,* 3:850-856 (2001); Kang et al., *J. Virol.,* 76:9378-9388 (2002)]. Three weeks later the animals were killed and the liver tissues examined for beta-galactosidase expression. Widespread expression was observed throughout the liver samples. This tropism for liver is useful for the production of secreted proteins or treatment of disorders primarily involving liver parenchyma, such as the mucopolysaccharidoses.

Example 4

Targeting Cells in the CNS with LCMV Pseudotyped FIV

The inventors evaluated the gene transfer properties of FIV pseudotyped with the LCMV-WE54 strain GP in the murine CNS. The plasmid LCMVgp.FIVβgal was introduced into the brain by striatal injection, and tissue samples were assessed for beta-gal labeling and staining with anti-NeuN antibodies, which served as markers for neurons. These experiments revealed that FIV pseudotyped with the envelope from LCMV strain WE54 (identical to WE-HPI) directs transgene expression in the OB after striatal injection, suggesting that neural progenitor cells in the subventricular zone (SVZ) were targeted. In support of this, transduced cells in the SVZ and the RMS also were noted, characteristic of progenitor cells and their progeny [Doetsch F, et al., *Proc. Natl. Acad. Sci. USA,* 96(20):11619-11624 (1999); Doetsch et al., *Cell,* 97(6):703-716 (1999); Alvarez-Buylla et al., *Brain Res. Bull.,* 57(6):751-758 (2002)]. There were no co-labeled beta-gal/NeuN$^+$ cells in the RMS or the SVZ. These very intriguing and exciting results indicated that pseudotyped LCMV vectors can be used to direct secretion of recombinant enzymes or growth factors from cells migrating along the rostral migratory stream for a beneficial effect. The results also suggest that such a strategy can be used to effect a substantial correction and functional recovery of CNS deficits in neurodegenerative or neurogenetic disorders such as lysosomal storage diseases (e.g., leukodystrophies, mucopolysaccharidoses, and ceroid lipofuscinoses), Huntington's disease, Parkinson's disease, amyotrophic lateral sclerosis, ataxias, dentatorubral-pallidoluysian atrophy, prion disease, and Alzheimer's disease. The method can also be used to transduce cells that are capable of dividing within the brain.

TABLE 1

Glycoproteins used for FIV brain gene transfer: predominant cell type transduced.

| VSV-G | gp64 | RRV | LCMV |
| --- | --- | --- | --- |
| neurons | neurons, neuroglia, ependyma, CP | glia | progenitor cells (SVZ), neurons (OB) |

CP, choroid plexus
SVZ, subventricular zone
OB, olfactory bulb

Example 5

Targeting Neural Progenitor Cells with LCMV Pseudotyped FIV

Plasmids and vector production: In this study, four replication-incompetent FIV vectors were generated. VSV-G/FIV-CMVntbeta-gal is pseudotyped with the VSV-G envelope, and the CMV promoter drives expression of ntbeta-gal.

LCMV/FIV-CMVntbeta-gal is LCMV pseudotyped and the CMV promoter drives expression of ntbeta-gal. LCMV/FIV-CMVbeta-gal is the same as the previous vector except that the beta-gal is cytoplasmic; and LCMV/FIV-GFAPcre is LCMV-pseudotyped and the GFAP promoter drives expression of cre recombinase.

FIV vectors were generated essentially as described [Stein and Davidson, *Meth. Enzymol.*, 346:433-454 (2002)] by triple transfection of 293T cells with the gag-pol-rev packaging plasmid, the env plasmid, and the vector plasmid. The parental plasmid used to construct the vector plasmids was pVETLCmcs, which contains a multiple cloning site (mcs) downstream of the CMV promoter. pVETLCmcs was derived from pVETLCα [Johnston et al., *J. Virol.*, 73:4991-5000 (1999)] by replacing the lacz gene (β) with the mcs. Coding regions for ntbeta-gal and beta-gal were subcloned into the mcs of pVETLCmcS to generate the pFIVCMVntbeta-gal and pFIVCMVbeta-gal vector plasmids, respectively. To generate the pFIVGFAPcre vector plasmid, modifications were first made to pVETLCmcs. The major splice donor site was mutated from GT to AT, and the RRE was moved from its native 3' location to a site just upstream of the CMV, to generate pFIVdSDrreC. The CMV promoter was removed from pFIVdSDrreC and replaced with the human GFAP promoter sequence to generate pFIVGFAP. The source of the GFAP promoter, pGfa2LAC-1, was kindly provided by Michael Brenner (University of Alabama, Birmingham, Ala.). This plasmid contains sequences −2163 to +47 of the human GFAP gene, in which the ATG has been mutated to TTG at position +15 (GenBank Accession No. M67446) [Besnard et al., *J. Biol. Chem.*, 266:18877-18883 (1991)]. The Bacteriophage P1 cre recombinase coding region (GenBank Accession No. X03453) with a PCR-primer generated Kozak sequence (ACCATG) was digested from pVETLCMVcre [Sinnayah et al., *Physiol. Genomics*, 18:25-32 (2004)], and inserted into pFIVGFAP, immediately downstream of the GFAP promoter to generate pFIVGFAPcre. The env plasmid encoding the LCMV envelope glycoprotein of the WE54 strain, which is the same as WE-HPI (GenBank Accession No. AJ318512) [Beyer et al., *J. Virol.*, 76:1488-1495 (2002)], was kindly provided by Winfried R. Beyer (Heinrich-Pette Institute, Hamburg, Germany). All vectors were concentrated from culture supernatants by centrifugation. Visual titers for beta-gal and ntbeta-gal vectors were determined as described (Stein and Davidson, supra) by limiting-dilution transduction of HT1080 cells and X-gal staining, and are expressed as transducing units/ml (TU/ml). Real-time PCR titers (integrating Units/ml, IntU/ml) for vectors were determined by isolation of genomic DNA from transduced HT1080 cells (Wizard kit, Promega Corp, Madison, Wis.) and quantifying integrated vector sequences.

Animals and Injections: C56BL6/J mice were purchased from The Jackson Laboratory (Bar Harbor, Me.) or were bred in-house. ROSA26 Cre reporter mice [Soriano, *Nat. Genet.*, 21:70-71 (1999)], on a C57BL6 background were purchased from The Jackson Laboratory (stock #003474).

Initial experiments were performed by injecting VSV-G/FIV-CMVbeta-gal ($7.5 \times 10^9$ TU/ml) or LCMV/FIV-CM-Vntbeta-gal ($2.9 \times 10^8$ TU/ml) into the striatum of adult C57BL6/J mice. Injections were done as described [Stein and Davidson, supra], using coordinates of 0.4 mm rostral and 2 mm lateral to bregma, and 3.0 mm depth. Five microliters of vector preparation were injected at a speed of 500 nL per minute. For this experiment, 3 mice were injected with each vector, and were sacrificed at 3 weeks post-injection. In subsequent experiments, injection coordinates were adjusted to 1.0 mm rostral and 1.7 mm lateral to bregma and 2.5 mm depth for adult mice, or 0.8 mm rostral and 1.3 mm lateral to bregma and 2.0 mm depth for 3-week old mice. For the non-5-bromo-2'-deoxyuridine (BrdU) experiments, six 16-week old C57BL6/J mice and four 3-week old C57BL6/J mice were injected with LCMV/FIV-CMVbeta-gal ($6 \times 10^8$ TU/ml; $9.1 \times 10^9$ IntU/ml). Mice were sacrificed at either three weeks or 7.5 weeks post injection. For BrdU experiments, three adult mice were injected with LCMV/FIV-CMVbeta-gal on day 0, and received intraperitoneal (i.p.) injections of BrdU (150 mg/kg) daily for 18 days and were sacrificed 24 hours after the last BrdU injection. The BrdU (Sigma-Aldrich Inc., St. Louis, Mo.) was dissolved in 0.007 N NaOH/0.9% NaCl at 10 mg/ml. For experiments with ROSA26 Cre reporter mice, three adult mice were injected with LCMV/FIV-GFAPcre ($1.4 \times 10^9$ IntU/ml), and sacrificed at three weeks post-injection.

At sacrifice, mice were anaesthetized and perfused with 2% paraformaldehyde in phosphate-buffered saline, pH 7.4 (PBS). Brains were dissected out and post-fixed overnight at 4° C., cryo-protected by sinking in 30% sucrose/PBS for 36 to 48 hours at 4° C. and embedded in OCT freezing compound (Sakura Finetek USA, Torrance, Calif.). Ten μm cryosections were placed on glass-plus slides, and 40 μm cryosections (floating) were placed in PBS.

X-gal and Immuno-fluorescent staining: For histological detection of beta-galactosidase enzymatic activity, 10 μm cryosections on slides were stained with X-gal (Sigma-Aldrich) for 6 hours at 37° C. and counterstained with neutral red.

For immuno-fluorescent staining, the antibodies used were as follows: rabbit anti-beta-galactosidase (BioDesign International, Saco, Me.) kit-conjugated to alexa 488 (Molecular Probes Inc., Eugene, Oreg.) and used at 5 μg/ml; monoclonal mouse anti-NeuN (Chemicon International Inc., Temecula, Calif.) used at 1/200; Cy-3-conjugated monoclonal mouse anti-GFAP (Sigma) used at 1/5000; monoclonal mouse anti-class III beta-tubulin (TuJ1 clone, R&D Systems, Minneapolis, Minn.) used at 1/300; monoclonal rat anti-BrdU (Accurate Chemical & Scientific Corp., Westbury, N.Y.) used at 1/500; and appropriate alexa 568- or alexa 647-conjugated secondary antibodies from goat (Molecular Probes) used at 1/500. Ten-micrometer sections on slides or 40-μm floating sections were stained essentially as described [Stein and Davidson *Meth. Enzymol.*, 346:433-454 (2002)]. Briefly, sections were blocked with 10% normal goat serum in PBS/0.2% triton-X-100 (PBS-T) for 1-2 hours at room temperature, stained with primary antibodies diluted in PBS-T at 4° C. overnight (10 μm sections on slides) or for 48 hours (40-μm floating sections), washed with PBS and stained with secondary antibodies for 1 hour (10 μm sections) or 3 hours (40 μm sections) at room temperature, washed and coverslipped with Vectashield (Vector Laboratories Inc., Burlingame, Calif.). For BrdU staining, slides were blocked and stained with anti-beta-galalexa 488 overnight at 4° C., washed and acid-treated with 2N HCL in PBS-T for 30 minutes at 37° C., washed at room temperature with 0.1M sodium tetraborate (pH 8.5) followed by PBS, then re-blocked for 1 hour and stained overnight with anti-BrdU and either TuJ1 antibody or anti-NeuN at 4° C., then washed and stained with secondary antibodies as described. To estimate the number of BrdU positive neurons in the OB, beta-gal positive cells were counted in multiple OB fields in eight 10-μm sections at 100 μm intervals and scored as BrdU negative or positive.

Microscopic images were captured using a Spot RT camera and associated software (Diagnostic Instruments Inc., Sterling Heights, Mich.). Confocal images were captured on a Zeiss LSM 510 confocal microscope using LSM camera and software.

Pattern of Transgene Expression

A lentivirus vector pseudotyped with the LCMV WE-64 envelope glycoprotein and carrying a nuclear-targeted bacterial beta-galactosidase (ntbeta-gal) transgene driven by the cytomegalovirus (CMV) immediate early enhancer/promoter (LCMV/FIV-CMVntbeta-gal) was injected into the striatum of adult mice to assess the pattern of cell transduction in the brain. X-gal staining of para-sagittal sections at three weeks postinjection indicated that significant numbers of transgene-expressing cells were present not only in the striatum around the injection site, but also in the OB. This was unlike VSV-G-pseudotyped vector, which typically shows high level transduction in the striatum of predominantly neurons [Blomer et al., *J. Virol.*, 71(9):6641-6649 (1997); Wong et al., *Mol. Ther.*, 9:101-111 (2004); and Brooks et al., *Proc. Natl. Acad. Sci. USA* 99:6216-6221 (2002)], with relatively few transgene-expressing cells found in the OB.

In a subsequent experiment, 3- and 16-week old mice were injected with LCMV/FIV-CMVbeta-gal. Here the beta-gal was cytoplasmically localized, rather than nuclear targeted, thus allowing discernment of cell types on the basis of both morphology and confocal analysis after immuno-fluorescent staining for beta-gal and markers for astrocytes (GFAP), neurons (NeuN), or migratory neuroblasts (class III beta-tubulin). Using immuno-fluorescence beta-gal positive cells were detected in the striatum, SVZ, RMS, and OB at 3 weeks post-injection. This pattern was observed for both age groups of mice, but the extent of transgene-expressing cells was greater in the younger age group. By morphological criteria, most of transgene-expressing cells in the injected area of the striatum appeared to be astrocytes, while those in the OB appeared to be neurons. Notably, many of the neurons extended a single unbranched apical dendrite, characteristic of class 3 developing granule neurons described by Petreanu and Alvarez-Buylla, *J. Neurosci.*, 22:6106-6113 (2002). Confocal microscopy after dual immunofluorescent staining showed overlap of beta-gal and GFAP signals in the striatum, SVZ, and to a lesser extent in the proximal RMS, indicating that transgene-expressing cells near the injection site were predominantly astrocytes. In the horizontal (rostral) aspects of the RMS, overlap with GFAP was not apparent. Dual immunofluorescent staining for beta-gal and class III betatubulin, a marker expressed early in neuronal commitment and prominent in migratory neuroblasts, showed co-localization throughout the RMS, especially in the rostral aspects. This was evident at both 3 weeks and 7.5 weeks post gene transfer. Moreover, the morphology of the beta-gal expressing cells in the RMS was typical of migratory neuroblasts: elongated cells with a leading appendage and growth cone [Wichterle et al., *Neuron* 18:779-791 (1997)]. In the OB, confocal analysis showed that the beta-gal expressing cells contained NeuN positive nuclei, confirming their identity as neurons. This pattern of transgene expression was highly suggestive of transduction of SVZ neural progenitor cells that give rise to the neuronal precursors that migrate to and terminally differentiate in the OB.

BrdU Incorporation

To confirm that the OB neurons and their migratory precursors were indeed the progeny of proliferating progenitor cells, the nucleotide analog BrdU was injected into mice that had received unilateral LCMV/FIV-CMVbeta-gal injection in the brain striatum. BrdU was injected i.p. daily from day 1 through day 18 relative to vector injection on day 0, and mice were sacrificed 24 hours after the final BrdU dose. Confocal microscopy after triple staining for beta-gal, NeuN and BrdU, showed that BrdU-labeled and non-labeled beta-gal-expressing neurons were present in the OB. Approximately 49% of the transgene-expressing neurons in the OB were BrdU positive, while the rest were BrdU negative. Since BrdU was injected only once per day, the BrdU negative cells may have arisen from mitotically active precursors that escaped BrdU labeling. Alternatively, the BrdU$^-$/beta-gal$^+$ neurons in the OB may have arisen from precursors that were transduced at post-mitotic state. With respect to the triple positive cells (beta-gal$^+$/NeuN$^+$/BrdU$^+$), it is clear that cell division occurred after LCMV-mediated vector uptake, and thus these neurons in the OB were derived from a progenitor that underwent cell division after transduction. Similarly, BrdU$^+$/beta-gal$^+$ migratory neuroblasts were observed in the RMS, indicating the ongoing generation of neuroblasts from a mitotically active transduced stem cell/progenitor.

Type B Astrocytes are Transduced

The transduced cell type giving rise to the neuroblasts that traffic to the OB could be either a slowly dividing neural stem cell and/or a rapidly dividing progenitor cell. Doetsch and colleagues describe a GFAP-expressing type B astrocyte that has the properties of a neural stem cell [Doetsch et al., *Cell* 97:703-716 (1999)]. To determine whether this cell type is a target of the LCMV-pseudotyped FIV, an LCMV-pseudotyped FIV vector was constructed carrying the cre recombinase transgene under control of the GFAP promoter (LCMV/FIV-GFAPcre). LCMV/FIV-GFAPcre was injected unilaterally into the striatum of ROSA26 Cre reporter mice, which harbor "loxP-stop-loxP-lacz" sequences downstream of an endogenous, ubiquitous promoter. If type B astrocytes in the SVZ were transduced, this should have resulted in expression of cre recombinase and excision of the "stop" signals, leading to expression of beta-gal in the transduced cells and their progeny. The reporter mice were sacrificed 3 weeks after vector injection and para-sagittal sections were analyzed by confocal microscopy after immuno-fluorescent staining. Beta-gal positive cells were detected within the SVZ, RMS, and the OB of the LCMV/FIV-GFAPcre-injected mice. No beta-gal expressing cells were detected in the contralateral RMS or OB. Confocal analysis showed that beta-gal positive cells in the RMS were also class III beta-tubulin positive, while those in the OB co-localized with NeuN. Since cre is driven off the GFAP promoter, these cells must have descended from a transduced astrocyte. Together, the results indicate that the LCMV-pseudotyped vector transduced type B astrocytes, the leading candidate for neural stem cells in the SVZ.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated neural progenitor cell comprising a vector comprising a Lymphocytic Choriomeningitis Virus strain WE-54 envelope glycoprotein.

2. The neural progenitor cell of claim 1, wherein the vector further comprises a transgene.

3. The cell of claim 1, wherein the vector is a lentivirus.

4. The cell of claim 3, wherein the lentivirus is a feline immunodeficiency virus.

5. A method comprising inserting an LCMV envelope glycoprotein into a lipid vesicle, and electroporating plasmid DNA into the lipid vesicle.

* * * * *